United States Patent
Walters et al.

(10) Patent No.: US 7,754,667 B2
(45) Date of Patent: *Jul. 13, 2010

(54) LOW-IRRITATION COMPOSITIONS AND METHODS OF MAKING THE SAME

(75) Inventors: Russel M. Walters, Philadelphia, PA (US); Michael J. Fevola, Belle Meade, NJ (US); Joseph J. LiBrizzi, Hillsborough, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 445 days.

This patent is subject to a terminal disclaimer.

(21) Appl. No.: 11/429,522

(22) Filed: May 5, 2006

(65) Prior Publication Data

US 2007/0111910 A1    May 17, 2007

Related U.S. Application Data

(60) Provisional application No. 60/679,297, filed on May 10, 2005.

(51) Int. Cl.
*C11D 3/37* (2006.01)
*C11D 1/12* (2006.01)
*C11D 1/88* (2006.01)
*C11D 9/32* (2006.01)
*A61K 8/23* (2006.01)
*A61K 8/73* (2006.01)

(52) U.S. Cl. .............. 510/127; 510/155; 510/158; 510/159; 510/426; 510/434; 510/470; 510/473; 510/476; 510/477; 510/492; 424/401; 424/487; 424/70.5; 424/70.16; 424/70.22; 424/70.24

(58) Field of Classification Search .............. 510/127, 510/155, 158, 159, 426, 434, 470, 473, 476, 510/477, 492; 424/401, 487, 70.5, 70.16, 424/70.22, 70.24
See application file for complete search history.

(56) References Cited

U.S. PATENT DOCUMENTS

| | | | |
|---|---|---|---|
| 4,110,263 A | 8/1978 | Lindemann et al. |
| 4,186,113 A | 1/1980 | Verdicchio et al. |
| 4,215,064 A | 7/1980 | Lindemann et al. |
| 4,228,277 A | 10/1980 | Landoll |
| 4,233,192 A | 11/1980 | Lindemann et al. |

(Continued)

FOREIGN PATENT DOCUMENTS

DE    19818410 A1    10/1999

(Continued)

OTHER PUBLICATIONS

U.S. Appl. No. 10/922,668, filed Aug. 19, 2004, Joseph Librizzi, A1.

(Continued)

*Primary Examiner*—Brian P Mruk

(57) ABSTRACT

Provided are compositions comprising low molecular weight polymeric materials and surfactants having reduced irritation associated therewith, methods of reducing the irritation associated with a personal care composition comprising an anionic and/or amphoteric surfactant, the methods comprising combining a low molecular weight polymeric material capable of binding a surfactant thereto with an anionic surfactant to produce a reduced irritation personal care composition, and methods of using such compositions to cleanse the hair or skin with reduced irritation.

32 Claims, 10 Drawing Sheets

U.S. PATENT DOCUMENTS

| | | | |
|---|---|---|---|
| 4,256,611 A | 3/1981 | Egan et al. | |
| 4,263,178 A | 4/1981 | Guth | |
| 4,372,869 A | 2/1983 | Lindemann et al. | |
| 4,380,637 A | 4/1983 | Lindemann et al. | |
| 4,382,036 A | 5/1983 | Lindemann et al. | |
| 4,443,362 A | 4/1984 | Guth et al. | |
| 4,552,685 A * | 11/1985 | Kernstock et al. | 510/535 |
| 4,617,414 A | 10/1986 | Lukenbach et al. | |
| 4,726,915 A | 2/1988 | Verdicchio | |
| 4,948,576 A | 8/1990 | Verdicchio et al. | |
| 5,004,557 A | 4/1991 | Nagarajan et al. | |
| 5,373,044 A | 12/1994 | Adams et al. | |
| 5,661,189 A | 8/1997 | Grieveson et al. | |
| 5,792,739 A | 8/1998 | He et al. | |
| 5,876,705 A | 3/1999 | Uchiyama et al. | |
| 6,001,344 A | 12/1999 | Villa et al. | |
| 6,172,019 B1 | 1/2001 | Dehan et al. | |
| 6,433,061 B1 | 8/2002 | Marchant et al. | |
| 6,642,198 B2 | 11/2003 | Pflederer et al. | |
| 6,737,394 B2 | 5/2004 | Shana'a et al. | |
| 7,098,180 B2 * | 8/2006 | Ganopolsky et al. | 510/476 |
| 7,119,059 B2 * | 10/2006 | Librizzi et al. | 510/476 |
| 7,157,414 B2 * | 1/2007 | Librizzi et al. | 510/127 |
| 7,417,020 B2 * | 8/2008 | Fevola et al. | 510/475 |
| 2002/0123438 A1 * | 9/2002 | Pflederer et al. | 510/119 |
| 2003/0026775 A1 | 2/2003 | Marchesi et al. | |
| 2003/0103929 A1 | 6/2003 | Maubru | |
| 2003/0108578 A1 | 6/2003 | Maubru | |
| 2003/0147827 A1 * | 8/2003 | Decoster et al. | 424/70.12 |
| 2003/0171230 A1 * | 9/2003 | Shana'a et al. | 510/130 |
| 2004/0001792 A1 | 1/2004 | Biatry | |
| 2004/0042990 A1 | 3/2004 | Biatry | |
| 2004/0047824 A1 | 3/2004 | Biatry | |
| 2004/0052739 A1 | 3/2004 | Biatry | |
| 2004/0091441 A1 | 5/2004 | Heike et al. | |
| 2004/0175342 A1 | 9/2004 | Biatry | |
| 2005/0070453 A1 | 3/2005 | Librizzi et al. | |
| 2007/0017553 A1 * | 1/2007 | Neplenbroek et al. | 134/25.2 |

FOREIGN PATENT DOCUMENTS

| | | |
|---|---|---|
| DE | 100 57 925 A1 | 5/2002 |
| DE | 10057925 A | 5/2002 |
| EP | 1 192 938 A2 | 4/2002 |
| EP | 1 374 852 A1 | 1/2004 |
| EP | 1374852 A | 1/2004 |
| WO | WO 03/074021 A | 9/2003 |
| WO | WO 03/074021 A1 | 9/2003 |
| WO | WO 03/084499 A | 10/2003 |
| WO | WO 03/084499 A2 | 10/2003 |
| WO | WO 2004/006870 A | 1/2004 |
| WO | WO 2004/006870 A2 | 1/2004 |

OTHER PUBLICATIONS

U.S. Appl. No. 10/959,272, filed Oct. 4, 2004, Arup Bhattacharyya, A1.

Bernhofer, et al., *Toxicology in Vitro*, The Influence of the Response of Skin Equivalent Systems to Topically Applied Consumer Products by Epithelial-Mesenchymal Interactions 219-229 (1999).

Carbopol® Aqua SF-1 Polymer, Brilliant Gold Pearlized 2-In-1 Conditioning Shampoo Formulation, Noveon, Inc. CASF1-001, Dec. 2000.

Carbopol® Aqua SF-1 Polymer, Pearlized 2-in-1 Conditioning Shampoo formulation, Noveon, Inc., CASF1-002, Nov. 19, 2001.

Carbopol® Aqua SF-1 Polymer, Clear Shampoo Formulation, Noveon, Inc., CASF1-003, Dec. 2000.

Carbopol® Aqua SF-1 Polymer, Bath Gel with Vitamin E Moisturizing Beads Formulation, Noveon, Inc., CASF1-004, Dec. 2000.

Carbopol® Aqua SF-1 Polymer, Pearlized Mild Body Wash Formulation, Noveon, Inc., Cas F1-005, Nov. 19, 2001.

Carbopol® Aqua SF-1 Polymer, Clear Bath Gel (High Betaine) Formulation, Noveon, Inc., CASF1-006, Dec. 2000.

Carbopol® Aqua SF-1 Polymer, Anti-Dandruff Shampoo Formulation, Noveon, Inc., CASF1-007, Dec. 2000.

Carbopol® Aqua SF-1 Polymer, Clear Shampoo/Bath Gel with Beads Formulation, Noveon, Inc., CASF1-008, Mar. 29, 2002.

Carbopol® Aqua SF-1 Polymer, Salicylic Acid Shampoo Formulation, Noveon, Inc., CASF1-009, Dec. 2000.

Carbopol® Aqua SF-1 Polymer, Salicylic Acid Facial Scrub Formulation, . Noveon, Inc., CASF1-010, Feb. 25, 2002.

Carbopol® Aqua SF-1 Polymer, Temporary Hair Color shampoo (Medium Brown) Formulation, Noveon, Inc., CASF1-011, Dec. 2000.

Carbopol® Aqua SF-1 Polymer, Antibacterial Liquid Hand Soap with suspended Beads Formulation, Noveon, Inc., CASF1-012, Dec. 2000.

Carbopol® Aqua SF-1 Polymer, Clear Facial Cleanser Formulation, Noveon, Inc., CASF1-013, Dec. 2000.

Carbopol® Aqua SF-1 Polymer, Clear Hydrating Body Wash with Suspended Beads Formulation, Noveon, Inc.; CASF1-014, Nov. 19, 2001.

Carbopol® Aqua SF-1 Polymer, Sprayable d-Limonene Waterless Hand Cleaner Formulation, Noveon, Inc., CASF1-015, Jan. 2001.

Carbopol® Aqua SF-1 Polymer, Body Lotion Formulation, Noveon, Inc., CASF1-016, Dec. 2000 .

Carbopol® Aqua SF-1 Polymer, Facial Cream Formulation, Noveon, Inc., CASF1-017, Dec. 2000.

Carbopol® Aqua SF-1 Polymer, Alpha Hydroxy Acid Cream Formulation, Noveon, Inc., CASF1-018, Dec. 2000.

Carbopol® Aqua SF-1 Polymer, Pearlized 3-In-1 Conditioning Shampoo Formulation, Noveon, Inc., CASF1-019, Nov. 19, 2001.

Carbopol® Aqua SF-1 Polymer, Clear Shampoo with Microcapsules Formulation, Noveon, Inc., CASF1-020, Dec. 2000.

Carbopol® Aqua SF-1 Polymer, Clear Baby Shampoo Formulation, Noveon, Inc., CASF1-021, Dec. 2000.

Carbopol® Aqua SF-1 Polymer, Economy Pearlized 3-in-1 Conditioning Shampoo Formulation, Noveon, Inc., CASF1-022, Jan. 2001.

Clear Conditioning Shampoo Using Ultrasil™ Q-Plus and Ultrasil™ A-23 Silicones, Noveon, Inc., SIL-019, Dec. 12, 2002.

Clear Bath Gel (High Betaine) Using Carbopol® Aqua Sf-1 Polymer, Noveon, Inc., CASF1-024EU, Feb. 10, 2003.

Clear Shampoo/Bath Gel with Beads Using Carbopol® Aqua SF-1 Polymer, Noveon, Inc., CASF1-025EU, Feb. 26, 2003.

Brilliant Gold Pearlized 2-in-1 Conditioning Shampoo Using Carbopol® Aqua SF-1 Polymer, Noveon, Inc., CASF1-026EU, Feb. 26, 2003.

Ethnic Hair Moisturizing Cream With Ultracas™ G-20, Noveon, Inc., SIL-0002, Jun. 28, 2001.

Antibacterial Hand Wash with Moisturizers Using Ultrasil™ Dw-l8 Silicone, Noveon, Inc., SIL-0005, Mar. 1, 2002.

Mild Conditioning Cream Shampoo, Noveon, Inc., SIL-0017, Dec. 12, 2002.

Moisturizing Shampoo for Ethnic Hair, Noveon, Inc., SIL-0020, Feb. 26, 2003.

Aveeno® Stress Relief Foaming Bath Formulation, Johnson & Johnson Consumer Companies, Inc., 2003.

Aveeno® Daily Moisturizing Foatning Bath Formulation, Johnson & Johnson Consumer Companies, Inc., 2003.

Aveeno® Positively Radiant™ Cleanser Formulation, Johnson & Johnson Consumer Companies, Inc., 2003.

Johnson's® Softwash™ Baby Shampoo Formulation, Johnson & Johnson Consumer Companies, Inc., 2002.

Johnson's® Softwash™ Baby Wash Formulation, Johnson & Johnson Consumer Companies, Inc., 2002.

Johnson's® Soothing Skin Baby Bath Formulation, Johnson & Johnson Consumer Companies, Inc., 2001.

Invittox Protocol No. 86, "The Trans-Epithelial Permeability (TEP) Assay," (May 1994).

Moore, et al., Challenging the surfactant monomer skin penetration model: Penetration of sodium dodecyl sulfate micelles into the epidermis (Journal of Cosmetic Science), Nov. 15, 2002, pp. 29-45.

Moore, et al., Penetration of mixed micelles into the epidermis: Effect of mixing sodium dodecyl sulfate with dodecyl hexa (ethylene oxide) (Journal of Cosmetic Science), 54, 2003, pp. 143-159.

Lubrizol, Molecular Weight of Carbopol® Polymers, Oct. 15, 2007, pp. 1-3, Lubrizol Advanced Materials, Inc. Cleveland, Ohio.

Lubrizol, Molecular Weight of Carbopol® Polymers, Oct. 15, 2007, pp. 1-3, Lubrizol Advanced Materials, Inc., Cleveland, Ohio.

European Search Report dated Dec. 21, 2004 for EP appln. 04254988.1.

European Search Report dated Dec. 21, 2004 for EP appln. 04254989.9.

European Search Report dated Dec. 21, 2004 for EP appln. 04254987.3.

European Search Report dated Dec. 21, 2004 for EP appln. 04254990.7.

International Search Report dated Dec. 17, 2004 for PCT/US04/27317.

Chevron Phillips, Specialty Chemicals, "Polyanhydride Resins" [online] 2009 [retrieved on Sep. 25, 2009] from http://www.cpchem.com/enu/specialtychemicalspolyanhydrideresins.asp.

Chevron Phillips, MSDS "PA-18" [online] Nov. 08, 2005 [retrieved on Sep. 25, 2009] from http://www.cpchem.com/enu/msds_unsecured/ImportPE0090MSDSOENGLISH_AENGLISHAN.pdf.

* cited by examiner

PA-18/CAPB

Inutec SP-1/TDES

PA-18/TDES

Inutec SP-1 / SLES

PA-18 / SLES

Rheology

LOW-IRRITATION COMPOSITIONS AND METHODS OF MAKING THE SAME

CROSS-REFERENCE TO RELATED APPLICATION

This application claims the benefit and priority of provisional U.S. application Ser. No. 60/679,297 titled "METHODS OF REDUCING IRRITATION IN PERSONAL CARE COMPOSITIONS", filed on May 10, 2005.

FIELD OF INVENTION

The present invention relates to compositions having low irritation characteristics, methods for reducing the irritation characteristics associated with a variety of personal care compositions, and methods of using such compositions.

DESCRIPTION OF THE RELATED ART

Synthetic detergents, such as cationic, anionic, amphoteric, and non-ionic surfactants, are used widely in a variety of detergent and cleansing compositions to impart cleansing properties thereto. In addition, in certain compositions (e.g. personal care compositions such as shampoos, washes, etc.), it may be desirable to use combinations and levels of surfactants sufficient to achieve relatively high levels of foam volume and/or foam stability.

However, as is recognized in the art, synthetic detergents tend to be irritating to the skin and eyes. Thus, as levels of such detergents are increased in attempts to increase cleansing and foaming properties associated with certain compositions, the irritation associated with such compositions also tends to increase, making them undesirable for use on or near the skin and/or eyes.

Certain attempts to produce milder cleansing compositions have included combining relatively low amounts of anionic surfactants (which tend to be relatively high-foaming but also relatively highly irritating), with relatively lower irritating surfactants such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, mild cleansing compositions produced via both of such methods tend to suffer from relatively poor foaming and cleansing performance.

Accordingly, applicants have recognized the need for alternative methods of reducing the irritation associated with cleansing compositions and new low irritation compositions. In addition, in certain embodiments, applicants have recognized the need for compositions that are not only mild to the skin and/or eyes, but additionally exhibit desirable foam properties and/or other desirable aesthetic properties.

SUMMARY OF THE INVENTION

The present invention provides mild cleansing compositions and methods of reducing the irritation associated with a variety of personal care compositions, which compositions and methods overcome the disadvantages of the prior art. In particular, according to certain preferred embodiments of the present invention, applicants have discovered advantageously that polymeric materials capable of binding surfactant thereto and having a relatively low molecular weight, as compared to composition comprising comparable, higher-molecular-weight polymers, can be combined with surfactants comprising surfactant selected from the group consisting of anionic surfactants, amphoteric surfactants, and combinations of two or more thereof, to produce personal care compositions exhibiting surprisingly low irritation to the skin and/or eyes. In certain embodiments, the mild compositions of the present invention additionally exhibit relatively high-foaming/foam stability properties, and/or unique viscosity characteristics.

Accordingly, one aspect of the present invention provides for methods of reducing the irritation associated with a personal care composition comprising an anionic and/or amphoteric surfactant, the method comprising combining a polymeric material capable of binding surfactant thereto and having a molecular weight of less than about 10,000,000 g/mol with an anionic surfactant to produce a reduced irritation personal care composition.

According to another aspect of the present invention, provided are compositions produced according to the present invention, that is, compositions comprising a surfactant selected from the group consisting of anionic surfactants, amphoteric surfactants, and combinations of two or more thereof, and a polymeric material capable of binding the surfactant thereto, the polymeric material having a molecular weight of less than about 10,000,000 g/mol.

According to yet another aspect of the present invention, provided are methods of cleansing a portion of the human body with reduced irritation thereto comprising the step of contacting the body of a mammal with a reduced irritation composition comprising an anionic and/or amphoteric surfactant and a polymeric material capable of binding the surfactant thereto and having a molecular weight of less than about 10,000,000 g/mol.

DESCRIPTION OF PREFERRED EMBODIMENTS

Figure 1:
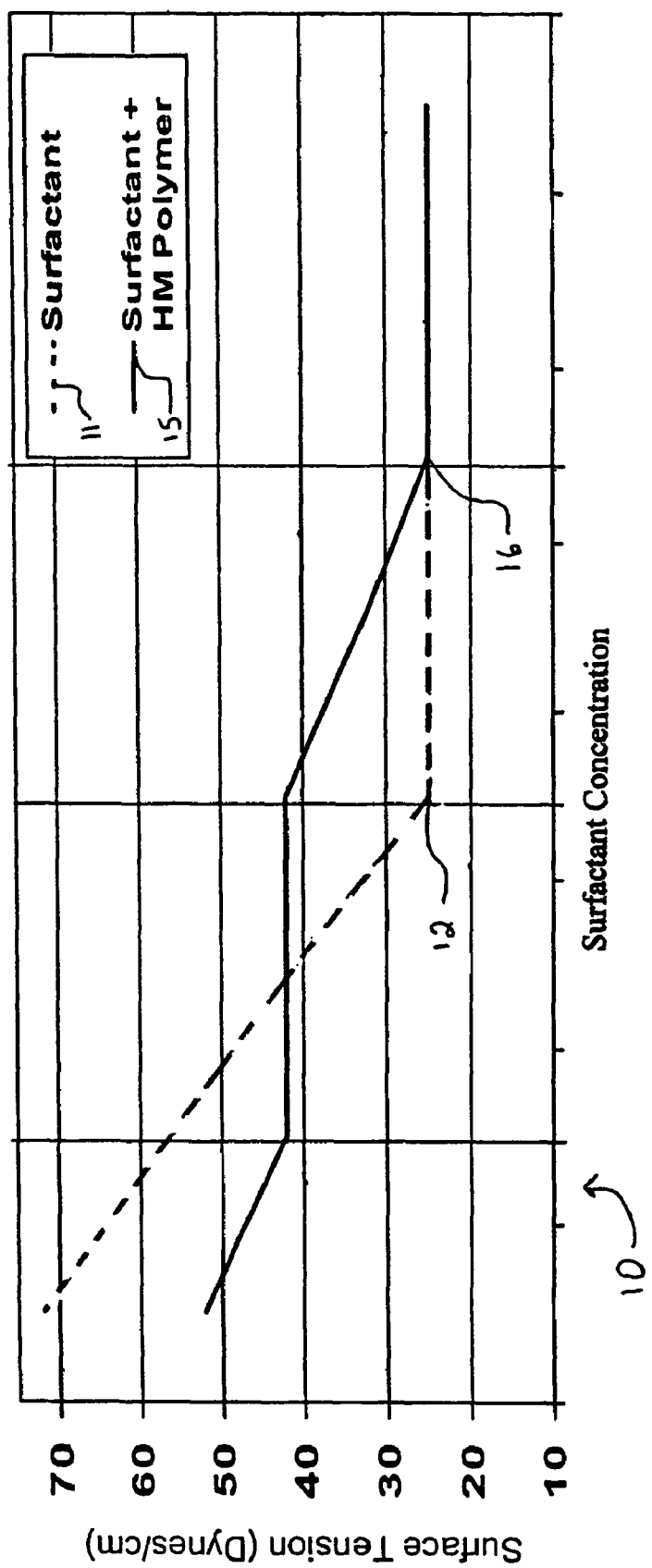
FIG. 1 is a graphical depiction of the idealized tensiometry data associated with the addition of anionic surfactant to two solutions.

As used herein the term "low molecular weight" polymer refers to a polymer having a weight average molecular weight of less than about 10,000,000 grams per mole ("g/mol").

Certain preferred low molecular weight polymers include polymers having a weight average molecular weight of from about 1,500 to about 10,000,000 g/mol. Certain more preferred low molecular weight polymers include polymers having a weight average molecular weight of from about 2,500 to about 5,000,000 g/mol, more preferably from about 3,000 to about 1,000,000 g/mol, more preferably from about 3,500 to about 500,000. In certain particularly preferred embodiments, the low molecular weight polymers include polymers having a weight average molecular weight of from about 3,500 to about 100,000 g/mol, more preferably about 3,500 to about 60,000 g/mol, in certain embodiments preferably about 5,000 to about 60,000 g/mol, and more preferably from about 15,000 to about 50,000.

While applicants have previously discovered certain types of hydrophobically-modified materials useful for reducing irritation in personal care compositions (examples of which are disclosed in U.S. application Ser. Nos. 10/650,226, 10/650,495, 10/650,573, 10/650,398, all filed on Aug. 28, 2003, and U.S. application Ser. Nos. 10/922,668, 10/959,275, and 10/922,669, filed Aug. 19, 2004, and each of which is incorporated herein by reference in its entirety), applicants have now further discovered that relatively low molecular weight polymeric compositions, including low molecular weight hydrophobically modified polymers, and other materials, can be used in the present compositions and methods to more effectively and efficiently reduce irritation, as compared to relatively higher molecular weight polymers, even at higher levels of added polymer.

For example, applicants have measured the ability of low-molecular weight polymers of the present invention, and comparable higher molecular weight polymers, to associate surfactants thereto (via Delta CMC measurement, described below, wherein higher Delta CMC indicates higher association of surfactant to polymer), and plotted such measurements as a function of polymer concentration in FIGS. 2-4 to illustrate the relative efficiency of the polymers of the present invention in associating surfactant. As illustrated in FIG. 2, applicants have discovered unexpectedly that while high molecular weight polymer materials (e.g. a high molecular weight acylic polymer designated "SF-1" in the Fig.) tend to lose efficiency in reducing irritation as the concentration of polymeric material in a composition is increased beyond a certain point, the relatively low molecular weight polymers of the present invention (e.g. a low molecular weight [octa-decene/methacrylate] octadecene/maleic anhydride copolymer designated "PA-18" and a low molecular weight polysaccharide polymer designated "Inutec SP-1" shown in the FIG. 1) tend not to exhibit the same loss of efficiency at high concentrations. That is, graph 20 is a plot of the delta CMC (CMC shift) of compositions comprising polymeric material and sodium trideceth sulfate ("TDES") against the increase of polymeric material for: (a) a low molecular weight material "Inutec SP-1" 21, (b) low molecular weight material "PA-18" 22 and a comparative plot for the higher molecular weight "SF-1" material 23. Curves 21 and 22 are relatively more linear, showing relatively little (or less) loss of efficiency for shifting CMC and lowering irritation as the concentration of polymer increases, whereas the curve 23 is relatively more non-linear showing a maximum concentration of high molecular weight polymer after which the ability to shift CMC and reduce irritation is reduced.

In addition, applicants have further measured the relative efficiency of the present polymers and comparative polymers via the $C_{90}$ Measurement, described below, wherein a higher $C_{90}$ value indicates a relatively higher range of concentrations over which a polymer associates surfactant thereto, and thus tends to more efficiently reduce irritation associated with a resulting composition comprising the polymer and surfactant. Applicants have discovered that the polymers of the present invention tend to exhibit $C_{90}$ values that are greater than 1.5 times, in certain embodiments about 1.7 times or greater, and in certain embodiments about 2 times or greater, than the $C_{90}$ values associated with higher molecular weight polymers. In particular, applicants have discovered that certain low molecular weight polymers are suitable for use with anionic and/or amphoteric surfactants to achieve a $C_{90}$ value of greater than about 250 mg/L. In certain preferred embodiments, the polymers of the present invention are suitable for use with anionic and/or amphoteric surfactants to achieve a $C_{90}$ value of about 300 mg/L or greater, more preferably about 350 mg/L or greater, more preferably about 400 mg/L or greater, more preferably about 450 mg/L or greater, and even more preferably about 500 mg/L or greater. Accordingly, in light of the above, applicants have discovered the present invention provides significant unexpected advantage in producing compositions having relatively low-irritation properties associated therewith.

Although applicants do not wish to be bound by or to any particular theory of operation, it is believed that the low molecular weight polymeric materials suitable for use in the instant methods act to reduce the irritation associated with personal care compositions; at least in part, by binding surfactant (free (unbound) surfactant molecules and/or, especially, surfactant free (unbound) micelles) thereto to reduce the concentration of irritation-causing free micelles available in the composition to irritate the skin and/or eyes. That is, applicants have recognized that the relative amounts of surfactant free micelles contained in a particular composition affect the relative irritation to the skin and/or eyes associated with that composition, wherein higher amounts of free micelles tend to cause higher levels of irritation and lower levels of free micelles tends to cause less irritation. By binding surfactant and/or surfactant micelles thereto, the polymeric materials reduce the concentration of unbound surfactant micelles in a composition and allow for a higher concentration of surfactant to be added to the composition before free micelles are formed and/or before a particular level of irritation is achieved. This desirable shift in the concentration of surfactant required prior to the formation of free micelles is illustrated further in FIG. 1.

Figure 2:
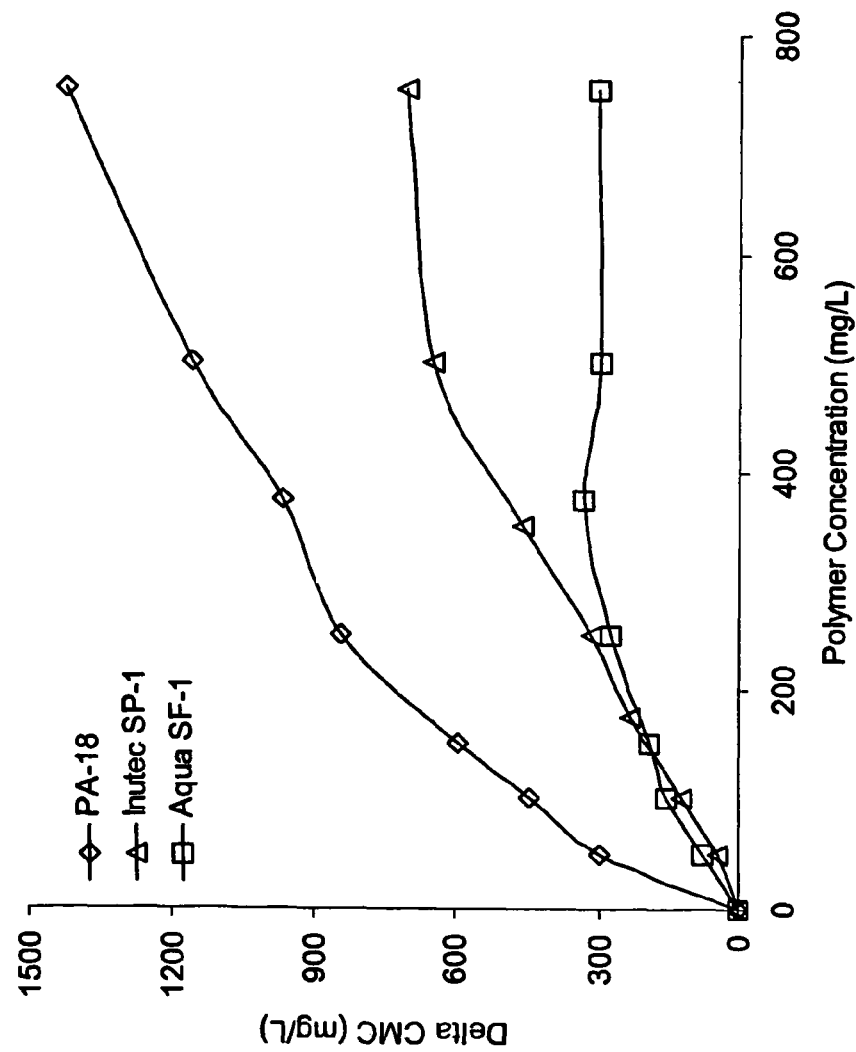
FIG. 2 is a graphical depiction of the relative efficiency of two polymers of the present invention, and a comparative polymer, to associate surfactant thereto according to certain embodiments.

FIG. 1 is a graph 10 showing the idealized surface tension data curves associated with the addition of anionic surfactant to two compositions, a composition comprising a polymeric material of the present invention and a comparable composition composition free of polymeric material. Curve 11 shows the change in surface tension, measured via conventional tensiometry techniques (examples of which are described hereinbelow), of a composition free of polymeric material as increasing levels of anionic surfactant are added thereto. Curve 15 shows the change in surface tension of a composition comprising polymeric material as increasing levels of anionic surfactant are added thereto. In curve 11, as surfactant is added to solution, the surfactant tends to populate the liquid/air interface, thus reducing the surface tension of the solution, until essentially the entire surface area is filled. After this point, hereinafter the "critical micelle concentration (CMC)" of surfactant, point 12, essentially all surfactant added to the composition forms free micelles in solution, which formation does not have an appreciable affect on the surface tension of the solution, but tends to increase the irritation associated with the composition. By comparison, as shown in curve 15, as anionic surfactant is added to a solution comprising a polymeric material of the present invention, the surfactant both aligns itself on the liquid/air interface and binds to the polymeric material until the CMC, point 16, shifted to a significantly higher surfactant concentration as compared to curve 11, at which point the surfactant added tends form free micelles.

In light of the above, applicants have recognized that one measure of the efficacy of a particular low molecular weight polymeric material in binding surfactant thereto may be expressed as the "Delta CMC" achieved by combining the polymeric material with an anionic surfactant to form a reduced irritation composition. A "Delta CMC" as used herein is defined as the number obtained by: (a) determining the CMC for: (i) a particular composition of the present invention comprising anionic surfactant and low molecular weight material, and (ii) the "comparable composition" of the composition in (i), which CMC values are determined using either the Forward or Reverse Titration Tensiometry Test procedures defined in the Examples below; and (b) subtracting the CMC value obtained for composition (ii) from the value obtained for composition (i). As used herein, the "comparable composition" of a particular composition comprising anionic surfactant and polymeric material means a composition which consists of the same components in the same relative weight percents as the anionic surfactant/polymeric material composition with the exception that the polymer of the anionic surfactant/polymeric material composition is replaced in the comparable composition with the same relative weight percent of water. For example, the comparable composition for an anionic surfactant/polymeric material composition consisting of 7% anionic surfactant, 15% amphoteric surfactant, 5% low molecular weight polymer, 5% glycerin, and 68% water (wherein all percents are by weight based on the total weight of the composition) is a composition consisting of 7% anionic surfactant, 15% amphoteric surfactant, 5% glycerin, and 73% water. By way of further example, the capability of a particular polymer material to bind a particular surfactant thereto in accord with the present invention may also be readily determined by measuring the CMC values of a composition comprising just the polymeric material and the surfactant in solution (for example, 12% surfactant/3% low molecular weight polymer/85% water) and a comparable composition comprising just the surfactant in solution (for example, 12% surfactant/88% water) and subtracting the latter from the former to get a Delta CMC.

Applicants have now discovered that combinations of low molecular weight polymeric materials with anionic and/or amphoteric surfactants tend to result in significant positive delta CMC (and thus significant reduction in irritation) that is at least as good, if not better than the delta CMC (and reduction of irritation) associated with the addition of the higher molecular weight polymers. In particular, the low molecular weight polymer tends to have a delta CMC that is significantly greater, as much as about 1.7 to over 2 times greater, than the delta CMC of the higher molecular weight polymeric material. Accordingly, applicants have recognized that the low molecular weight materials of the present invention may be used advantageously to achieve greater and more efficient reduction in irritation as compared to higher molecular weight materials. In certain embodiments, it is preferred to select a low molecular weight material for use in the present methods such that the Delta CMC associated with the resulting reduced irritation composition is a positive value. In certain more preferred embodiments, the low molecular weight material is selected to achieve a reduced irritation composition having a Delta CMC of about +80 or greater, more preferably, about +100 or greater, even more preferably of about +120 or greater, even more preferably of about +200 or greater, and even more preferably of about +300 or greater. In certain other preferred embodiments, the low molecular weight polymer for use in the present invention is one which results in a Delta CMC of about +400 or greater, more preferably, about +450 or greater, even more preferably of about +500 or greater, and even more preferably of about +600 or greater.

Applicants have recognized that the "TEP value" associated with a particular composition, which value is measured conventionally via the Trans-Epithelial Permeability Test ("TEP Test") as set forth in the Invittox Protocol Number 86 (May 1994) incorporated herein by reference and described in further detail in the Examples below, has a direct correlation to the irritation to the skin and/or eyes associated with the composition. More specifically, a higher TEP value of a composition tends to indicate less irritation to the skin and eyes associated therewith as compared to a composition having a lower TEP value, which composition tends to cause higher levels of irritation to the skin and/or eyes. Applicants have recognized that the present methods are suitable for producing personal care compositions having surprisingly high TEP values/lower irritation associated therewith. For example, in certain embodiments, the present methods produce compositions having a TEP value of at least about 1.5 or greater. In certain more preferred embodiments, the composition produced according to the present methods exhibit a TEP value of at least about 2 or greater, more preferably, at least about 2.5 or greater, even more preferably, at least about 3 or greater, and still more preferably, at least about 3.5 or greater. In certain particularly preferred embodiments, the compounds exhibit a TEP value of at least about 4.0 or greater, and even more preferably, about 4.5 or greater.

Furthermore, to determine when, and to express the degree to which, a composition comprising an anionic surfactant and polymeric material produced via the present methods exhibits reduced irritation in comparison to a comparable composition free of the polymeric material, applicants herein define the term "Delta TEP" of a composition of the present invention as the value obtained by: (a) measuring the TEP values of: (i) the composition of the present invention comprising an anionic surfactant and polymeric material and (ii) the comparable composition for such composition; and (b) subtracting the TEP value of the comparable composition from the TEP value for the anionic surfactant/polymeric material composition. Certain preferred reduced irritation compositions of the present invention include those having a Delta TEP of at least about +0.5. Certain more preferred reduced irritation compositions include those having a Delta TEP of at least about +0.75, and more preferably at least about +1. Certain particularly preferred reduced irritation compositions include those having a Delta TEP that is at least about +1.2, more preferably at least about +1.5, and more preferably at least about +1.8.

As indicated above, applicants have discovered that a positive shift in CMC correlates to a higher TEP and lower irritation associated with a composition. Accordingly, as used herein the term "reduced irritation composition" refers generally to a composition comprising an anionic surfactant and one or more polymeric materials capable of binding surfactant thereto, which composition has a positive Delta CMC measured using the Reverse Titration Tensiometry Test and a positive Delta TEP value (i.e. the composition has higher TEP value than its comparable composition), measured via the Invittox Protocol incorporated herein. Certain preferred reduced irritation compositions exhibit combinations of the preferred Delta CMC and Delta TEP values disclosed above (and include any combinations of preferred, more preferred, and even more preferred values of at least one Delta CMC and at, least one Delta TEP).

Applicants have further recognized that the present invention allows for the production of compositions that exhibit not only reduced irritation, but also desirable rheology and/or foaming properties. In particular, applicants have discovered that while certain higher molecular weight polymers tend to increase the viscosity and the yield point associated with a composition as more polymer is added, the low molecular weight polymers of the present invention tend to have relatively small effect on the rheology of the compositions to which they are added. Accordingly, in certain embodiments, higher amounts of the present polymers may be added to more significantly reduce irritation without producing a composition that is too viscous for effective personal use.

According to certain embodiments, the compositions of the present invention exhibit foaming properties (for example, $F_{max}$, measured as described below) which are at least as good, and preferably better than comparable compositions. In certain preferred embodiments, the compositions of the present invention exhibit an $F_{max}$ of at least about 250 ml, more preferably at least about 300 ml, and more preferably at least about 350 ml or greater.

Any of a variety of relatively low molecular weight polymeric materials capable of binding surfactant thereto may be used in the present invention. Examples of suitable polymeric materials include low-molecular weight acrylic, polysaccharide, cellulose, starch polymers, other ethylenically-unsaturated polymers, polyesters, polycarbonates, polyanhydrides, polyamides, polyurethanes, polyureas, polyimides, polysulfones, polysulfides, combinations of two or more thereof, and the like. Examples of suitable low molecular weight acrylic polymers include hydrophobically-modified acrylic polymers, as well as other acrylic polymers, any of which may be formed via solution, suspension, precipitation, dispersion, emulsion, inverse emulsion, microemulsion, micellar polymerization methods, and combinations of two or more thereof. The acrylic polymers for use in the present invention may be derived from any one or more monomers selected from the group consisting of (meth)acrylates, (meth)acrylamides, vinyl ethers, esters, and amides, allyl ethers, esters, amines, and amides, itaconates, crotonates, styrenics, and olefins. The acrylic polymers may be nonionic hydrophilic, nonionic hydrophobic, anionic, cationic, zwitterionic, nonassociative macromer, associative macromer, or multifunctional/crosslinking.

As used herein, the term "hydrophobically-modified material" refers generally to any material having one or more hydrophobic moieties attached thereto or incorporated therein. Certain preferred hydrophobically-modified materials include materials having a hydrophobe comprising 6 carbons ($C_6$) or more, preferably 8 carbons ($C_8$) or more, more preferably from 10 to 16 carbons ($C_{10-16}$). Examples of certain types of preferred hydrophobically-modified materials include hydrophobically-modified polymers. Such polymers may be formed, for example, by polymerizing one or more hydrophobic monomers and, optionally, one or more co-monomers, to form a polymer having hydrophobic moieties incorporated therein, and/or also by reacting polymer materials with compounds comprising hydrophobic moieties to attach such compounds to the polymers. Certain hydrophobically-modified polymers and methods of making such polymers are described in U.S. Pat. No. 6,433,061, issued to Marchant et al. and incorporated herein by reference.

Low molecular weight hydrophobically-modified acrylic polymers suitable for use in the present invention may be in the form of random, block, star, graft copolymers, and the like. In certain embodiments, the hydrophobically-modified acrylic polymers are anionic acrylic copolymers. Such copolymers may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least 3 carbon atoms.

In one preferred embodiment, the hydrophobically-modified, anionic acrylic copolymer includes those compositions derived from at least one unsaturated carboxylic acid monomer; at least one hydrophobic monomer; a hydrophobic chain transfer agent comprising alkyl mercaptans, thioesters, amino acid-mercaptan-containing compounds or peptide fragments, or combinations thereof; a cross-linking agent; and, optionally, a steric stabilizer; wherein the amount of said unsaturated carboxylic acid monomer is from about 60% to about 98% by weight based upon the total weight of said unsaturated monomers and said hydrophobic monomer, as set forth in U.S. Pat. No. 6,433,061, which is incorporated by reference herein.

In another preferred embodiment, the low molecular weight hydrophobically-modified acrylic polymer is an associative macromer having a backbone derived from methacrylate and ethylacrylate, and a hydrophobic portion derived from itaconate monomers, which polymer is made via emulsion polymerization. Another preferred low molecular weight material comprises an [octadecene/methacrylate] octadecene/maleic anhydride alternating copolymer, having a molecular weight of from about 20,000 to about 25,000, available from Chevron Phillips Chemical as "PA-18", as well as derivatives of such polymer including hydrolyzed and amidated derivatives, and the like.

Examples of other suitable low molecular weight polymers include polysaccharides, preferably hydrophobically-modified polysaccharides, including those derived from cellulose, starch, inulin, guar, xanthan, carrageenan, chitosan, pectin, schizophyllan, and the like. Any of such polysaccharides may be nonionic hydrophilic, nonionic hydrophobic, anionic, cationic, zwitterionic, or polymeric.

Any of a variety of hydrophobically-modified inulin polysaccharides are suitable for use herein. Certain preferred hydrophobically-modified polysaccharides include those described generally by the formulas:

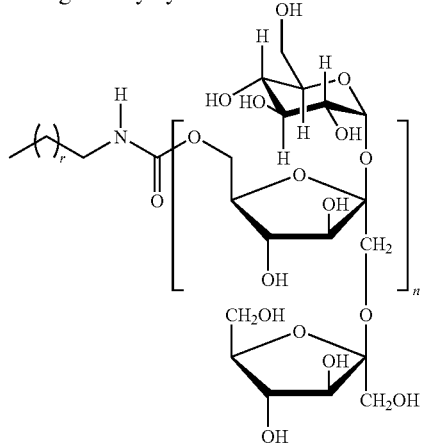

(GFn)

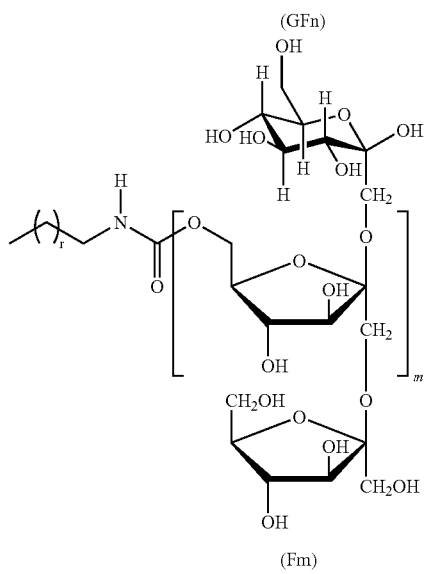

(Fm)

wherein m is about 15-10,000, more preferably about 15-1,000, more preferably about 10-300; n is about 5-10,000, more preferably about 15-1,000, more preferably about 10-300; and r is about 6-30, more preferably about 8-24, and more preferably about 8-18. The hm-inulin is a hm-polyfructose that is extracted from the roots of chicory (Cichorium intybus). Naturally according inulin is a polydisperse polysaccharide consisting mainly of β(2–1) fructosyl fructose units with normally, but not necessarily, one glucopyranose unit at the reducing end. The inulin is hydrophobically modified with alkyl groups ($C_4$-$C_{18}$) that are randomly distributed on the sugar backbone on the primary hydroxyl functions as well as on the secondary ones. An example of a preferred inulin polymer is available commercially from Orafti as "Inutec SP-1". The hm-inulin Inutec-SP-1 has a degree of polymerization of about 50 and a molecular weight (Mw) of about 5000 g/mol. The hydrophobe alkyl chain on the backbone is a distribution of chain lengths with an average alkyl chain length of about $C_{12}$.

Any of a variety of hydrophobically-modified cellulosics or starches are suitable for use in the present invention. Examples of suitable hydrophobically-modified cellulosics include hydrophobically-modified hydroxyethyl cellulose (available commercially, for example, from Hercules Inc. (Wilmington, Del.) as "Natrosol Plus"), and the like. Examples of suitable hydrophobically-modified starches include hydrophobically-modified hydroxylpropyl starch phosphate (available commercially, for example, from National Starch (Bridgewater, N.J.) as "Structure XL"), and the like.

Any of a variety of anionic surfactants may be combined with low molecular weight polymeric material to form a reduced irritation composition according to preferred embodiments of the present methods. According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

alkyl sulfates of the formula

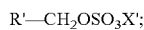
R'—CH$_2$OSO$_3$X';

alkyl ether sulfates of the formula

R'(OCH$_2$CH$_2$)$_y$OSO$_3$X';

alkyl monoglyceryl ether sulfates of the formula

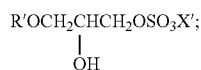
R'OCH$_2$CHCH$_2$OSO$_3$X';
|
OH alkyl monoglyceride sulfates of the formula

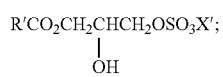
R'CO$_2$CH$_2$CHCH$_2$OSO$_3$X';
|
OH alkyl monoglyceride sulfonates of the formula

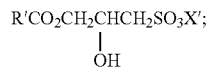
R'CO$_2$CH$_2$CHCH$_2$SO$_3$X';
|
OH alkyl sulfonates of the formula

R'—SO$_3$X';

alkylaryl sulfonates of the formula

alkyl sulfosuccinates of the formula:

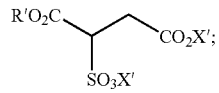

alkyl ether sulfosuccinates of the formula:

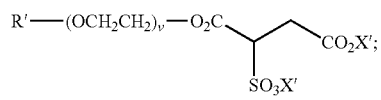

alkyl sulfosuccinamates of the formula:

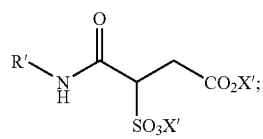

alkyl amidosulfosuccinates of the formula

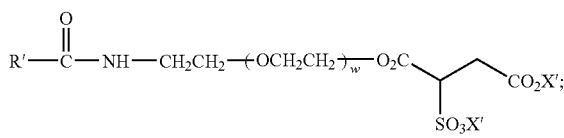

alkyl carboxylates of the formula:

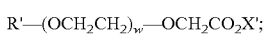
R'—(OCH$_2$CH$_2$)$_w$—OCH$_2$CO$_2$X';

alkyl amidoethercarboxylates of the formula:

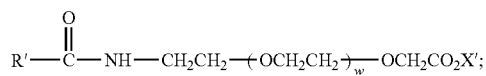

alkyl succinates of the formula:

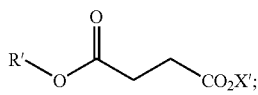

fatty acyl sarcosinates of the formula:

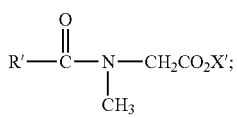

fatty acyl amino acids of the formula:

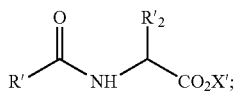

fatty acyl taurates of the formula:

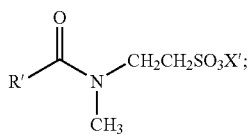

fatty alkyl sulfoacetates of the formula:

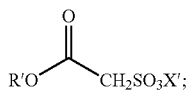

alkyl phosphates of the formula:

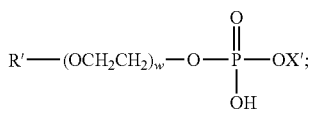

wherein

R' is an alkyl group having from about 7 to about 22, and preferably from about 7 to about 16 carbon atoms, $R'_1$ is an alkyl group having from about 1 to about 18, and preferably from about 8 to about 14 carbon atoms, $R'_2$ is a substituent of a natural or synthetic I-amino acid, X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and v is an integer from 1 to 6;

w is an integer from 0 to 20;

and mixtures thereof.

According to certain embodiments, the anionic surfactant of the present invention preferably comprises one or more alkyl ether sulfates, or mixtures thereof. In certain more preferred embodiments, the anionic surfactant of the present invention comprises sodium trideceth sulfate. Sodium trideceth sulfate is the sodium salt of sulfated ethoxylated tridecyl alcohol that conforms generally to the following formula, $C_{13}H_{27}(OCH_2CH_2)_nOSO_3Na$, where n has a value between 1 and 4, and is commercially available from Stepan Company of Northfield, Ill. under the tradename, "Cedapal TD-403M." Applicants have recognized that sodium trideceth sulfate can be used to particular advantage to obtain compositions having significantly reduced irritation associated therewith according to the present invention.

As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

wherein

A is an alkyl or alkenyl group having from about 7 to about 21, e.g. from about 10 to about 16 carbon atoms;

x is an integer of from about 2 to about 6;

$R_5$ is hydrogen or a carboxyalkyl group containing from about 2 to about 3 carbon atoms;

$R_6$ is a hydroxyalkyl group containing from about 2 to about 3 carbon atoms or is a group of the formula:

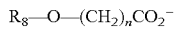

wherein $R_8$ is an alkylene group having from about 2 to about 3 carbon atoms and n is 1 or 2; and $R_7$ is a carboxyalkyl group containing from about 2 to about 3 carbon atoms;

Examples of suitable alkyl betaines include those compounds of the formula:

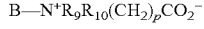

wherein

B is an alkyl or alkenyl group having from about 8 to about 22, e.g., from about 8 to about 16 carbon atoms;

$R_9$ and $R_{10}$ are each independently an alkyl or hydroxyalkyl group having from about 1 to about 4 carbon atoms; and p is 1 or 2.

A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula:

wherein

D is an alkyl or alkenyl group having from about 7 to about 21, e.g. from about 7 to about 15 carbon atoms;

$R_{11}$ and $R_{12}$ are each independently an alkyl or Hydroxyalkyl group having from about 1 to about 4 carbon atoms;

q is an integer from about 2 to about 6; and m is 1 or 2.

One amidoalkyl betaine is cocamidopropyl betaine, available commercially from Goldschmidt Chemical Corporation of Hopewell, Va. under the tradename, "Tegobetaine L7."

Examples of suitable amidoalkyl sultaines include those compounds of the formula

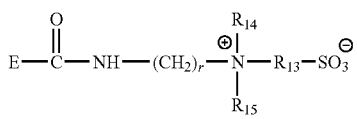

wherein

E is an alkyl or alkenyl group having from about 7 to about 21, e.g. from about 7 to about 15 carbon atoms;

$R_{14}$ and $R_{15}$ are each independently an alkyl, or hydroxyalkyl group having from about 1 to about 4 carbon atoms;

r is an integer from about 2 to about 6; and $R_{13}$ is an alkylene or hydroxyalkylene group having from about 2 to about 3 carbon atoms;

In one embodiment, the amidoalkyl sultaine is cocamidopropyl hydroxysultaine, available commercially from Rhone-Poulenc Inc. of Cranbury, N.J. under the tradename, "Mirataine CBS."

Examples of suitable amphophosphate compounds include those of the formula:

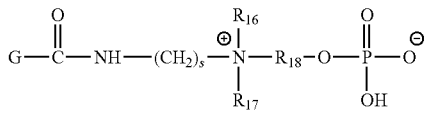

wherein

G is an alkyl or alkenyl group having about 7 to about 21, e.g. from about 7 to about 15 carbon atoms;

s is an integer from about 2 to about 6;

$R_{16}$ is hydrogen or a carboxyalkyl group containing from about 2 to about 3 carbon atoms;

$R_{17}$ is a hydroxyalkyl group containing from about 2 to about 3 carbon atoms or a group of the formula:

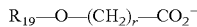

wherein $R_{19}$ is an alkylene or hydroxyalkylene group having from about 2 to about 3 carbon atoms and t is 1 or 2; and $R_{18}$ is an alkylene or hydroxyalkylene group having from about 2 to about 3 carbon atoms.

In one embodiment, the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.

Examples of suitable phosphobetaines include those compounds of the formula:

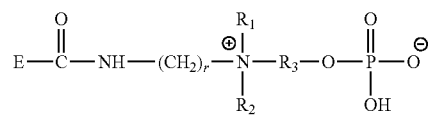

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

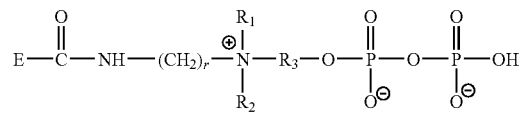

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

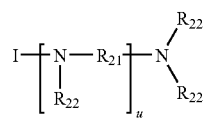

wherein

I is an alkyl or alkenyl group containing from about 8 to about 22, e.g. from about 8 to about 16 carbon atoms;

$R_{22}$ is a carboxyalkyl group having from about 2 to about 3 carbon atoms;

$R_{21}$ is an alkylene group having from about 2 to about 3 carbon atoms and u is an integer from about 1 to about 4.

Any amounts of low molecular weight polymeric materials and surfactants suitable to produce a reduced irritation composition may be combined according to the present methods. According to certain embodiments, sufficient low irritation polymeric material is used to produced a reduced irritation composition comprising from greater than zero to about 15% by weight of active low molecular weight polymeric material in the composition. Preferably, sufficient low molecular weight polymeric material is used to produce a reduced irritation composition comprising from about 0.1 to about 7%, more preferably from about 0.1 to about 5%, even more preferably from about 0.1 to about 4%, and even more preferably from about 0.1 to about 3% of active low molecular weight polymeric material in the composition. In certain other preferred embodiments, the compositions of the present invention comprise from about 0.5 to about 15%, more preferably from about 1.5 to about 10%, even more preferably from about 2 to about 7%, even more preferably from about 3 to about 7% of active low molecular weight polymeric material in the composition.

In embodiments comprising the use of anionic surfactant, the amount of anionic surfactant used in the present invention is preferably an amount sufficient to produce a reduced irritation composition comprising from about 0.1 to about 12.5%, more preferably from about 0.5 to about 8.5%, even more preferably from about 1 to about 8% of total active anionic surfactant in the composition. In certain other preferred embodiments, the amount of active anionic surfactant is an amount sufficient to produce a reduced irritation composition comprising from about 3.5 to about 7.3%, more preferably from 3.5% or greater to 7.3% or less, more preferably from 3.5% to 7%, and even more preferably from 4% to 7% of total active anionic surfactant in the composition.

In embodiments comprising the use of amphoteric surfactant, the amount of amphoteric surfactant used in the present invention is preferably an amount sufficient to produce a reduced irritation composition comprising from about 0.1 to about 12.5%, more preferably from about 0.5 to about 8.5%, even more preferably from about 1 to about 8% of total active amphoteric surfactant in the composition. In certain other preferred embodiments, the amount of active amphoteric surfactant is an amount sufficient to produce a reduced irritation composition comprising from about 3.5 to about 7.3%, more preferably from 3.5% or greater to 7.3% or less, more preferably from 3.5% to 7%, and even more preferably from 4% to 7% of total active amphoteric surfactant in the composition.

The low molecular weight polymeric material and anionic/amphoteric surfactant may be combined according to the present invention via any conventional methods of combining two or more fluids. For example, one or more compositions comprising, consisting essentially of, or consisting of at least one low molecular weight polymeric material and one or more compositions comprising, consisting essentially of, or consisting of at least one anionic and/or amphoteric surfactant may be combined by pouring, mixing, adding dropwise, pipetting, pumping, and the like, one of the compositions comprising low molecular weight polymeric material or surfactant into or with the other in any order using any conventional equipment such as a mechanically stirred propeller, paddle, and the like. According to certain embodiments, the combining step comprises combining a composition comprising anionic and/or amphoteric surfactant into or with a composition comprising low molecular weight polymeric material. According to certain other embodiments, the combining step comprises combining a composition comprising low molecular weight polymeric material into or with a composition comprising anionic and/or amphoteric surfactant.

The reduced irritation compositions produced, as well as any of the compositions comprising low molecular weight polymeric material or anionic and/or amphoteric surfactant that are combined in the combining step according to the present methods may further comprise any of a variety of other components nonexclusively including one or more non-ionic and/or cationic surfactants, pearlescent or opacifying agents, thickening agents, secondary conditioners, humectants, chelating agents, and additives which enhance the appearance, feel and fragrance of the compositions, such as colorants, fragrances, preservatives, pH adjusting agents, and the like.

Any of a variety of nonionic surfactants are suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "Atlas G4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Henkel Corporation of Hoboken, N.J. under the tradename, "Plantaren 2000."

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

Any of a variety of commercially available secondary conditioners, such as volatile silicones, which impart additional attributes, such as gloss to the hair are suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent or from about 0.05 percent to about 0.10 percent.

The methods of the present invention may further comprise any of a variety of steps for mixing or introducing one or more of the optional components described hereinabove with or into a composition comprising a low molecular weight polymeric material and/or an anionic and/or amphoteric surfactant either before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising a low molecular weight polymeric material and/or an anionic surfactant.

The reduced irritation compositions produced via the present invention are preferably used as or in personal care products such as shampoos, washes, baths, gels, lotions, creams, and the like. As discussed above, applicants have discovered unexpectedly that the instant methods allow for the formulation of such personal care products having reduced irritation to the skin and/or eyes and optionally other combinations of desirable aesthetics.

According to certain other preferred embodiments, the present invention provides methods for treating and/or cleansing a portion of the body, including the skin, hair, teeth, vagina, and the like, preferably the skin or hair, with reduced irritation thereto comprising the step of contacting the body of a mammal with a reduced irritation composition of the present invention.

Any conventional means for contacting the body, preferably mammalian skin and/or hair, can be used according to the present invention. In certain preferred embodiments, the contacting step comprises applying a reduced irritation composition of the present invention to human skin and/or human hair.

The cleansing methods of the present invention may further comprise any of a variety of additional, optional steps associated conventionally with cleansing hair and skin including, for example, lathering, rinsing steps, and the like.

EXAMPLES

The following Trans-Epithelial Permeability ("TEP"), Tensiometry tests, and $C_{90}$ Measurements are used in the instant methods and in the following Examples. In particular, as described above, the TEP test is used to determine when a composition is a reduced irritation composition according to the present invention, and the Tensiometry test and $C_{90}$ Measurements may be used to determine the suitability and/or efficiency of a particular polymeric material for binding surfactant thereto.

Trans-Epithelial Permeability Test ("TEP Test"):

Irritation to the eyes and/or skin expected for a given formulation is measured in accordance with the Invittox Protocol Number 86, the "Trans-epithelial Permeability (TEP) Assay" as set forth in Invittox Protocol Number 86 (May 1994), incorporated herein by reference. In general, the ocular and/or skin irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Tensiometry Titration Test:

A well-known method to measure the surface tension of surfactant solutions is the Wilhelmy plate method (Holmberg, K.; Jonsson, B.; Kronberg, B.; Lindman, B. *Surfactants and Polymers in Aqueous Solution*, Wiley & Sons, p. 347). In the method, a plate is submerged into a liquid and the downward force exerted by of the liquid on the plate is measured. The surface tension of the liquid can then be determined based on the force on the plate and the dimensions of the plate. It is also well known that by measuring the surface tension over a range of concentrations the critical micelle concentration (CMC) can then be determined.

There are commercially available Wilhelmy plate method instruments. In the following examples, a Kruss K12 Tensiometer (Kruss USA, Mathews, N.C.) with a platinum Wilhelmy plate used to determine the surface tension of each sample over a range of concentrations. The test can be run either forward or reverse. In either case, a sample vessel contains some initial solution in which the Wilhelmy plate measures the surface tension. Then a second solution is dosed into the sample vessel, stirred, and then probed again with the Wilhelmy plate. The solution initially in the sample vessel before the titration begins, into which the second solution is dosed, will be referred to hereinafter as the initial solution, and the solution that is dosed into the sample vessel during the titration will be referred to hereinafter as the dosing solution, in accordance with the convention used by Kruss USA.

In the forward titration, the concentration of the initial solution is lower than the concentration of the dosing solution. During forward titration tests, the initial solution was HLPC grade water (Fischer Scientific, NJ), with no surfactant. The dosing solution was a solution of surfactant to be associated with the polymer and HLPC grade water (Fischer Scientific, NJ) with a concentration of 5750 mg/L of surfactant. A large stock solution, 4 L, of the dosing surfactant solution was prepared before hand; the surfactant was added to HLPC grade water (Fischer Scientific, NJ) to a concentration of 5750 mg/L.

At the beginning of the forward titration, 30 ml of initial solution was added to the sample vessel. The surface tension of this initial solution was measured, and then a volume of the dosing solution was added to the sample vessel. The solution was stirred for at least 5 minutes, before the next surface tension measures was taken. All titrations were run from 0 mg/L to at least 3500 mg/L of the surfactant. A test run according to this procedure is here after referred to as a Forward Titration Tensiometry Test.

Alternatively in the reverse titration, the concentration of the initial solution is higher than the concentration of the dosing solution. During the reverse titration tests of the following examples, the dosing solution was HLPC grade water (Fischer Scientific, NJ), which had no surfactant, 0 mg/L. The full concentration formulas (for example, those in Table 5) were diluted with HLPC grade water (Fischer Scientific, NJ) to a dilution of approximately 5% wt. This 5% diluted solution was then added to the sample vessel and was the initial solution. The surface tension of this initial solution was measured, and then a volume of the dosing solution was added to the sample vessel. The solution was stirred for at least 5 minutes, before the next surface tension measures was taken. This dosing, stirring, and then measuring was repeated until the dilution reached at least 0.0008%. A Test run according to this procedure is here after referred to as a Reverse Titration Tensiometry Test.

Figure 9:
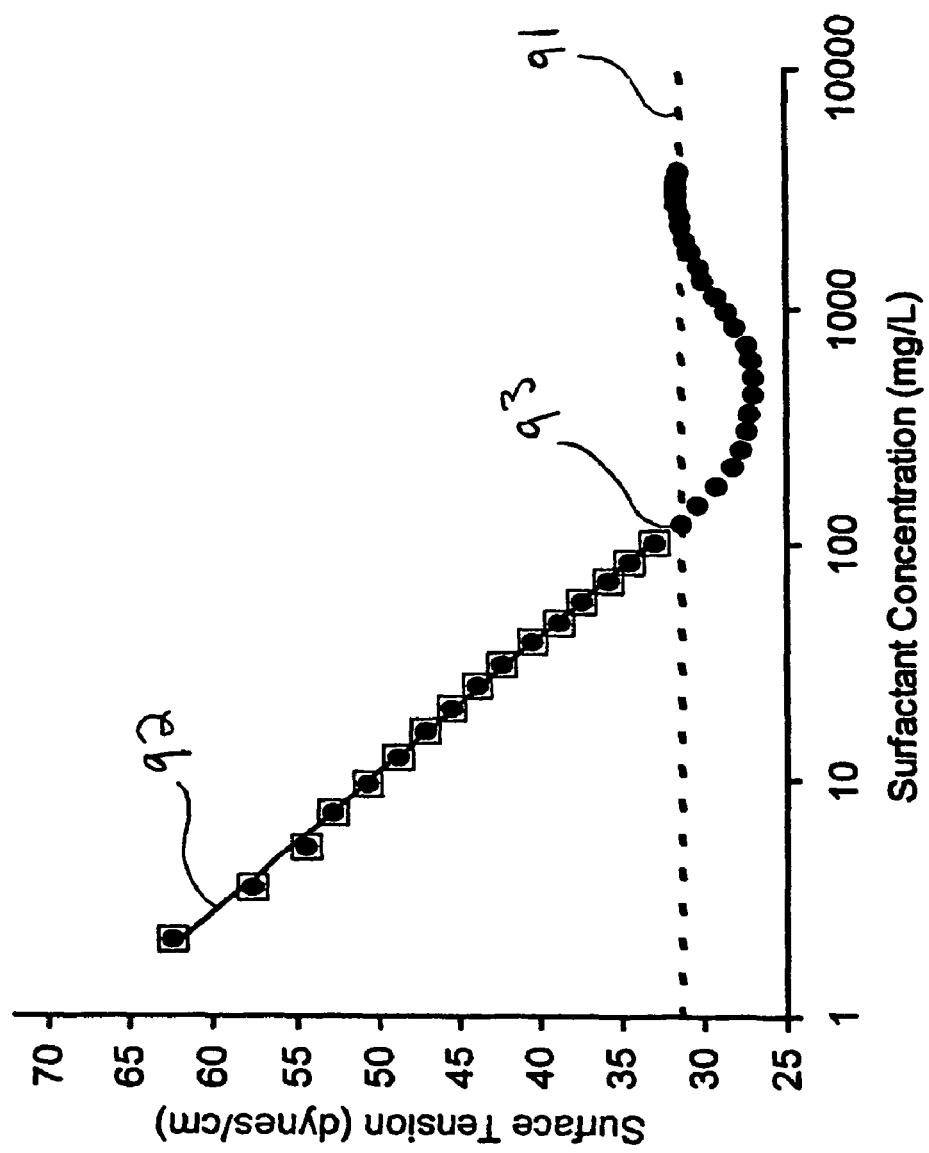
FIG. 9 is a graphical depiction of the tensiometry data associated with a composition of the present invention.

From the raw tensiometry data, the CMC was determined for each sample in the following manner. First, the equation for a horizontal line was fitted to the portion of the data at high concentrations, i.e. concentrations above the nadir of the graph and well into the region where the surface tension is essentially constant, as shown, for example, in FIG. 9 as line 91. Then, the equation for a straight line is fit to the data at lower concentrations having a surface tension above the horizontal line derived previously, as shown, for example, in FIG. 9 as line 92. The intersection of these two lines/equations 93 was then defined as the CMC for that sample.

$C_{90}$ Measurements

The $C_{90}$ attributed to a polymer for associating a surfactant thereto is calculated as follows. Eight compositions comprising the polymer in HPLC grade water at concentrations (in mg/L) of: 0, 50, 100, 175, 250, 375, 500 and 750 are prepared. The CMC associated with each composition with a particular surfactant are calculated via the Forward Tensiometry Titration test. The Delta CMC for each of the compositions comprising polymer are then calculated using such data. Based on such Delta CMC data and/or graphical representation of the Delta CMCs as a function of polymer concentration fit with an appropriate curve, the lowest concentration polymer composition which exhibits a Delta CMC value that is 90% of the Delta CMC value of the polymer composition having a concentration of 750 mg/L is determined, and such concentration value represents the $C_{90}$ value for such polymer and surfactant combination. Reference is made, for example, to the procedure in Example 1.

Example 1

The following example illustrates the efficiency of certain polymers of the present invention to associate surfactant thereto and reduce irritation as compared to higher molecular weight polymeric materials.

TDES

Compositions (E1-E14) comprising low-molecular weight polymers in water, and comparable compositions comprising no polymer or higher molecular weight polymers (C1-C8) were prepared as described below. The CMCs, Delta CMCs, and Delta CMC/750 for each composition with the surfactant sodium trideceth sulfate (TDES) were calculated using the Forward Titration Tensiometry Test as described below and the results reported in Table 2.

TABLE 1*

| Trade name | INCI Name | E1 | E2 | E3 | E4 | E5 | E6 | E7 |
|---|---|---|---|---|---|---|---|---|
| Inutec SP-1 | Inulin Lauryl Carbamate | 0.005 | 0.010 | 0.0175 | 0.025 | 0.0375 | 0.050 | 0.075 |
| Sodium Hydroxide (20%) | Sodium Hydroxide | — | — | — | — | — | — | — |
| DI Water | DI Water | Qs | Qs | Qs | Qs | Qs | Qs | qs |

| Trade name | INCI Name | E8 | E9 | E10 | E11 | E12 | E13 | E14 |
|---|---|---|---|---|---|---|---|---|
| PA-18 | Octadecene/MA Copolymer | 0.005 | 0.010 | 0.015 | 0.025 | 0.0375 | 0.050 | 0.075 |
| Sodium Hydroxide solution (20%) | Sodium Hydroxide | — | — | — | — | — | — | — |
| DI Water | DI Water | Qs | Qs | Qs | Qs | Qs | Qs | Qs |

| Trade name | INCI Name | C1 | C2 | C3 | C4 | C5 | C6 | C7 | C8 |
|---|---|---|---|---|---|---|---|---|---|
| Carbopol AQUA SF1 (30%) | Acrylates Copolymer | — | 0.005 | 0.010 | 0.015 | 0.025 | 0.0375 | 0.050 | 0.075 |
| Sodium Hydroxide solution (20%) | Sodium Hydroxide | As needed | As needed | As needed | As needed | As needed | As needed | As needed | As needed |
| DI Water | DI Water | Qs | Qs | Qs | Qs | Qs | Qs | Qs | qs |

*expressed in % w/w

The compositions of Table 1 were prepared as follows: HPLC grade water (50.0 parts) was added to a beaker. The polymer, if any, was added to the water with mixing. For the solutions containing Carbopol Aqua SF-1, the pH of each resulting solution was then adjusted with a 20% Sodium Hydroxide solution (as needed) until a final pH of about 7.0 was obtained. The remainder of the water was then added thereto.

Figure 5:
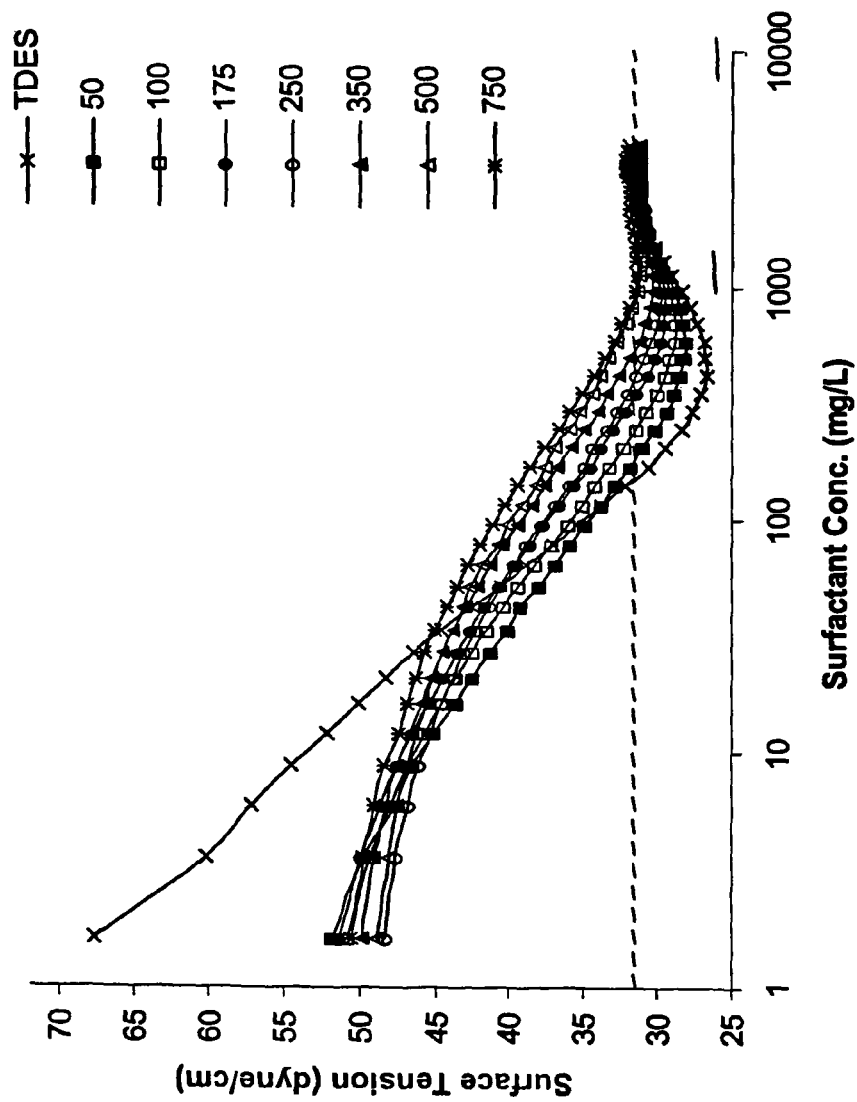
FIG. 5 is a graphical depiction of the tensiometry data for certain compositions according to one embodiment of the present invention and one comparative composition.
Figure 6:
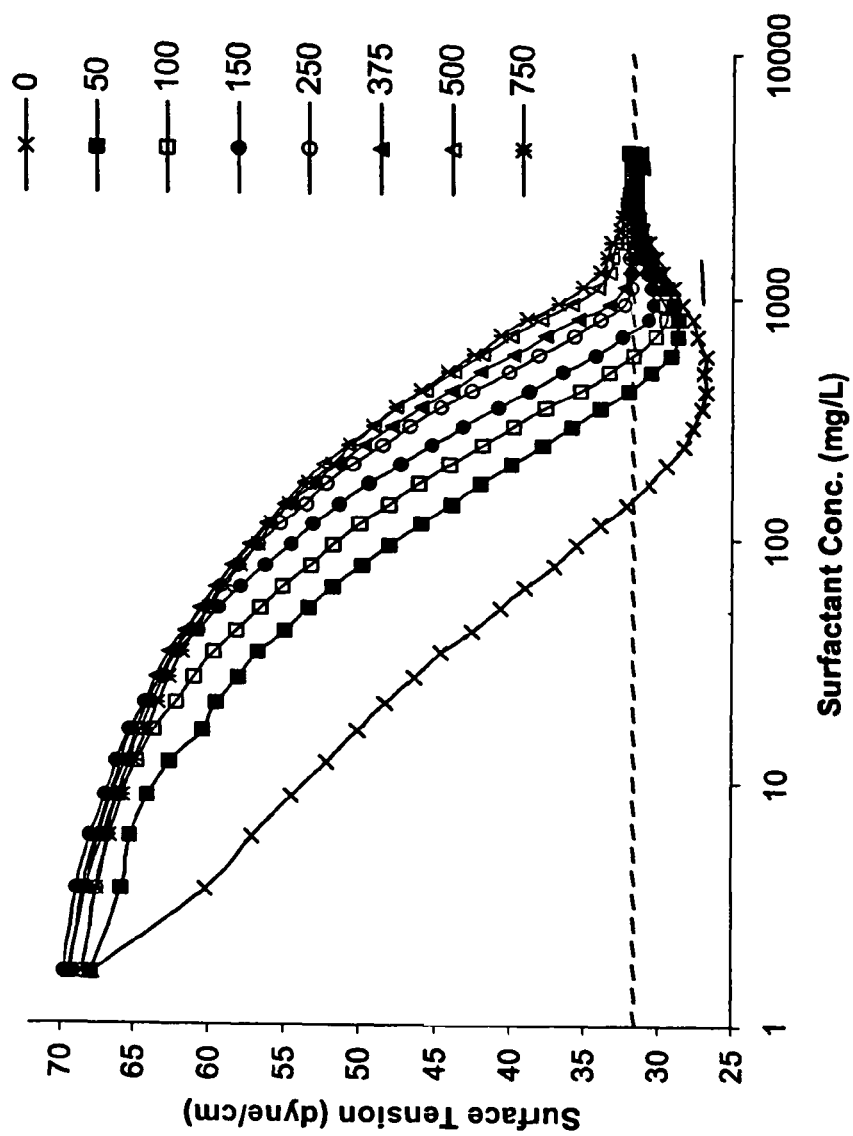
FIG. 6 is a graphical depiction of the tensiometry data for certain compositions according to another embodiment of the present invention and one comparative composition.
Figure 7:
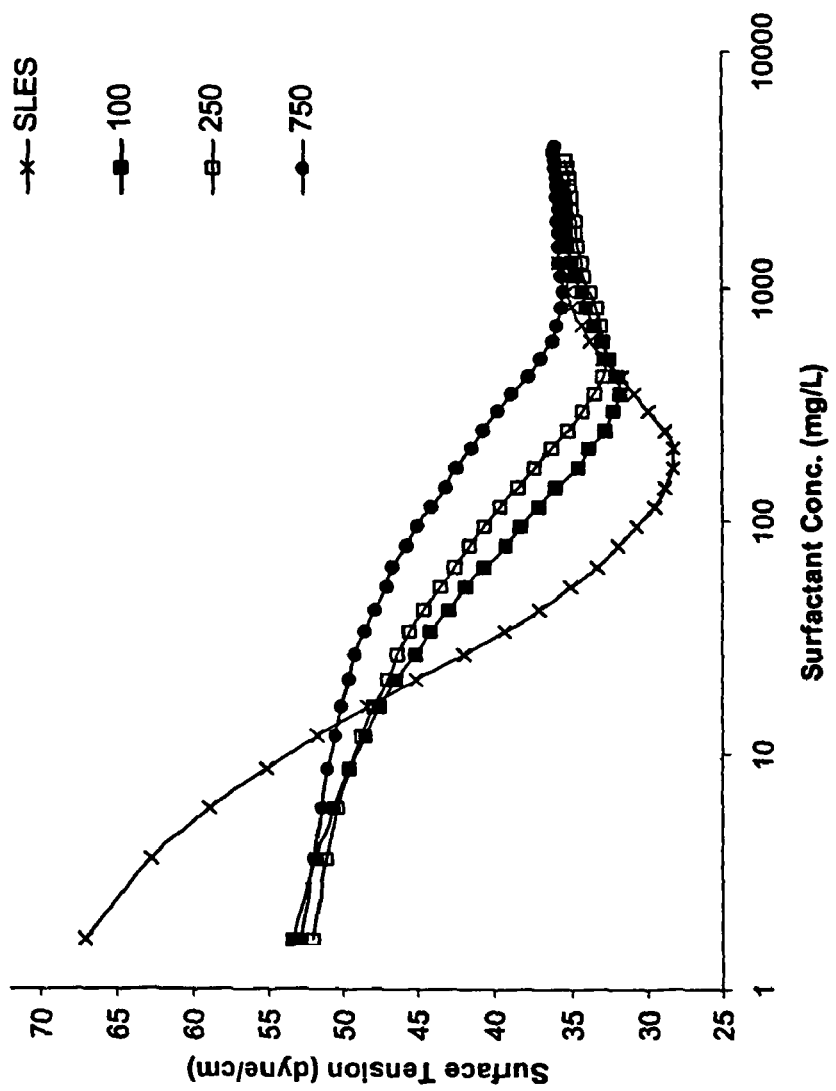
FIG. 7 is a graphical depiction of the tensiometry data for certain compositions according to another embodiment of the present invention and one comparative composition.
Figure 8:
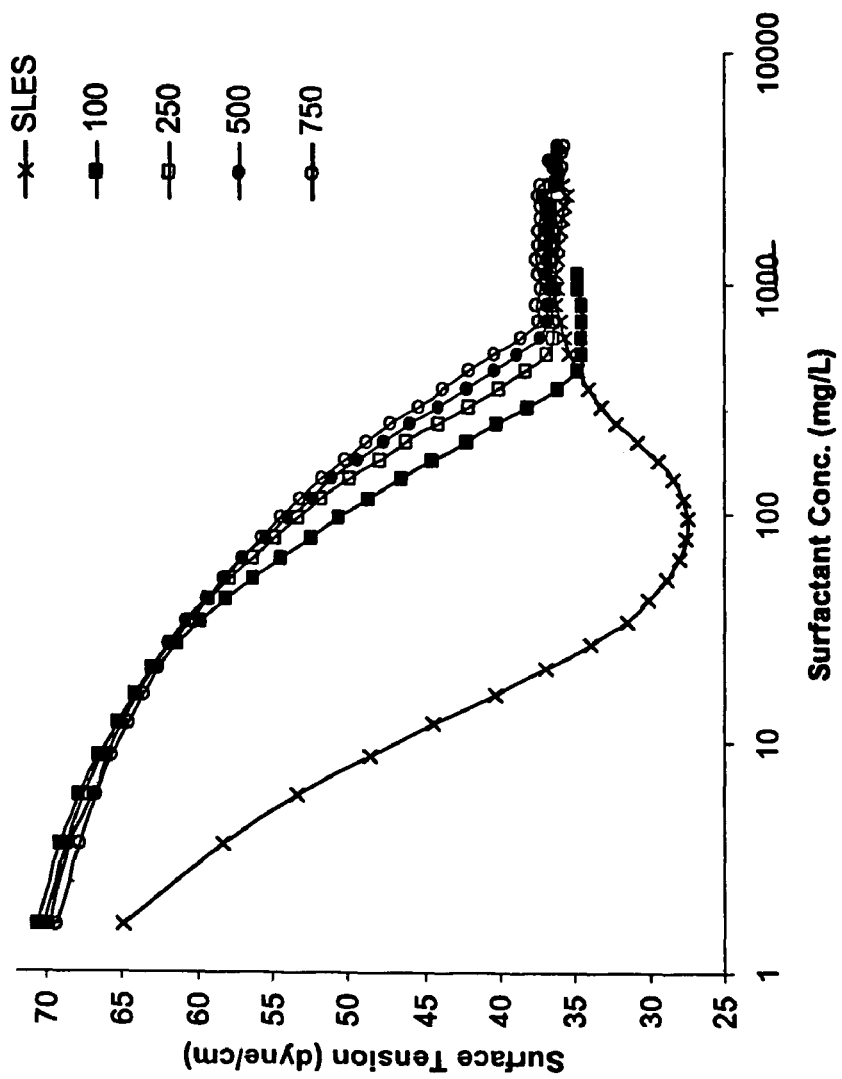
FIG. 8 is a graphical depiction of the tensiometry data for certain compositions according to another embodiment of the present invention and one comparative composition.

The compositions of Table 1 were tested for Critical Micelle Concentration (CMC) values using the Forward Titration Tensiometry Test. The initial solution was 30 ml of one of the Examples. The dosing solution was 5750 mg/L of sodium trideceth sulfate in HPLC grade water. Forty-two (42) doses were preformed, which increased the sodium trideceth concentration from 0 mg/L in the initial solution up to 3771 mg/L at the final measurement and the resulting tensiometry data plotted as shown in FIGS. 5 and 6. The Delta CMCs for each composition were calculated based on the CMC for comparable composition C1 and such values were plotted as a function of polymer concentration in FIG. 2 as an illustration of the efficiency of the polymers to associate surfactant thereto (and reduce irritation).

TABLE 2

| Composition | Inutec SP-1 (mg/L) | CMC TDES (mg/L) | Δ CMC TDES (mg/L) | Efficiency | Δ CMC/750% |
|---|---|---|---|---|---|
| C1 | 0 | 136 | na | na | na |
| E1 | 50 | 182 | 46 | 0.9 | 7 |
| E2 | 100 | 258 | 122 | 1.2 | 18 |
| E3 | 175 | 370 | 234 | 1.3 | 34 |
| E4 | 250 | 452 | 316 | 1.3 | 46 |
| E5 | 375 | 595 | 459 | 1.2 | 66 |
| E6 | 500 | 777 | 641 | 1.3 | 92 |
| E7 | 750 | 830 | 694 | 0.9 | 100 |

| Examples | PA-18 (mg/L) | CMC TDES (mg/L) | Δ CMC TDES (mg/L) | Efficiency | Δ CMC/750% |
|---|---|---|---|---|---|
| E8 | 50 | 434 | 298 | 6.0 | 21 |
| E9 | 100 | 582 | 446 | 4.5 | 32 |
| E10 | 150 | 730 | 594 | 4.0 | 42 |
| E11 | 250 | 961 | 838 | 3.4 | 59 |
| E12 | 375 | 1097 | 961 | 2.6 | 68 |
| E13 | 500 | 1289 | 1153 | 2.3 | 82 |
| E14 | 750 | 1550 | 1414 | 1.9 | 100 |

| Examples | Aqua SF-1 (mg/L) | CMC TDES (mg/L) | Δ CMC TDES (mg/L) | Efficiency | Δ CMC/750% |
|---|---|---|---|---|---|
| C1 | 0 | 136 | na | na | na |
| C2 | 50 | 213 | 77 | 1.5 | 26 |
| C3 | 100 | 291 | 155 | 1.6 | 52 |
| C4 | 150 | 328 | 192 | 1.3 | 64 |
| C5 | 250 | 410 | 234 | 1.1 | 92 |
| C6 | 375 | 468 | 274 | 0.9 | 111 |
| C7 | 500 | 431 | 295 | 0.6 | 99 |
| C8 | 750 | 434 | 298 | 0.4 | 100 |

Also shown in Table 2 for each of the compositions is the Efficiency, which is defined herein as the ratio of the Delta CMC (mg/L) to the polymer concentration. The Efficiency is a measure of how much surfactant the polymer associates at a given concentration.

To better assess the differences between the polymers in efficiency as polymer concentration is increased, also shown in Table 2 is ΔCMC/750, which is defined herein as the ratio of the ΔCMC at a particular concentration to the ΔCMC of a composition having a polymer concentration of 750 mg/L (times 100 to get a % value). The ΔCMC/750 provides a metric of the extent to which the polymer tends to loose efficiency as a function of concentration. For instance Aqua SF-1 reaches a ΔCMC/750 of 92% at a polymer concentration of only about 250 ml/L, while Inutec SP-1 does not reach a ΔCMC/750 of 92% until a polymer concentration of about 500 mg/L. This suggests that while a polymer concentration of Aqua SF-1 above 250 mg/L tends to provide relatively little additional TDES association, Inutec SP-1 is capable of associating relatively significant amounts of additional surfactant at concentrations greater than 500 mg/L. The "$C_{90}$ value" of a polymer and surfactant combination is the lowest polymer concentration at which the ΔCMC/750 of compositions comprising the polymer and surfactant, as measured via the Forward Titration Tensiometry Test as described hereinabove, is equal to 90%; As shown above, the $C_{90}$ value-associated with the comparable SF-1 polymer and TDES is less than about 250 mg/L, while the Inutec SP-1 polymer and TDES is greater than about 250 mg/L (about 500 mg/L) and the $C_{90}$ value associated with PA-18 and TDES is g greater than about 250 mg/L (and greater than about 500 mg/L).

Example 2

The following example illustrates the efficiency of certain polymers of the present invention to associate surfactant thereto and reduce irritation as compared to higher molecular weight polymeric materials.

The CMCs, Delta CMCs, Efficiency, and Delta CMC/750 for Compositions (E2, E4, E6, E7, E9, E11, E13, and E14) and comparable composition C1 with the surfactant sodium laureth sulfate (SLES) were calculated using the Forward Titration Tensiometry Test as described below and the results reported in Table 3.

The compositions were tested for Critical Micelle Concentration (CMC) values using the Forward Titration Tensiometry Test. The initial solution was 30 ml of one of the Examples. The dosing solution was 5750 mg/L of sodium laureth sulfate in HPLC grade water. Forty-two (42) doses were preformed, which increased the sodium trideceth concentration from 0 mg/L in the initial solution up to 3771 mg/L at the final measurement. The Delta CMCs for each composition were calculated based on the CMC for comparable composition C1 and such values were plotted as a function of polymer concentration in FIG. 3 as an illustration of the efficiency of the polymers to associate surfactant thereto (and reduce irritation).

TABLE 3

| Examples | CMC SLES (mg/L) | Δ CMC SLES (mg/L) | Efficiency | Δ CMC/750% |
|---|---|---|---|---|
| Inutec SP-1 (mg/L) | | | | |
| C1 | 0 | 42 | na | na | na |
| E2 | 100 | 116 | 74 | 0.7 | 19 |
| E4 | 250 | 176 | 135 | 0.5 | 34 |
| E6 | 500 | 332 | 291 | 0.6 | 73 |
| E7 | 750 | 439 | 398 | 0.5 | 100 |
| PA-18 (mg/L) | | | | |
| C1 | 0 | 42 | na | na | na |
| E9 | 100 | 322 | 279 | 2.8 | 42 |
| E11 | 250 | 1467 | 425 | 1.7 | 63 |
| E13 | 500 | 592 | 549 | 1.1 | 82 |
| E14 | 750 | 714 | 672 | 0.9 | 100 |

Figure 3:
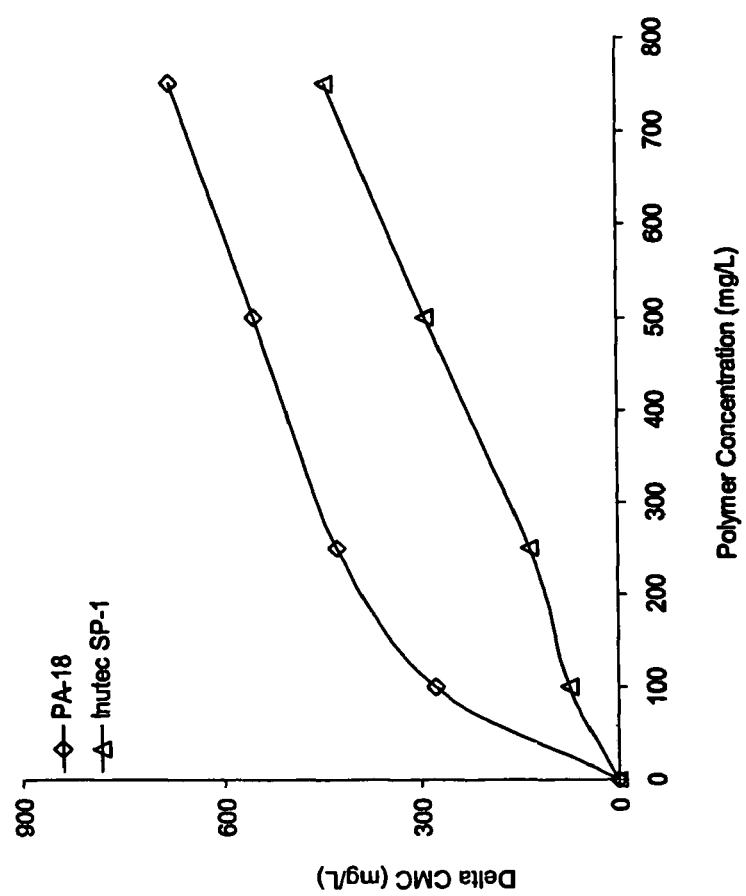
FIG. 3 is a graphical depiction of the relative efficiency of two polymers of the present invention to associate surfactant thereto according to certain other embodiments.

As shown in Table 3 and FIG. 3, the $C_{90}$ value associated with the Inutec SP-1 polymer and SLES, and PA-18 and SLES, are each greater than about 250 mg/L (and greater than 500 mg/L).

Example 3

The following example illustrates the efficiency of certain polymers of the present invention to associate surfactant thereto and reduce irritation as compared to higher molecular weight polymeric materials.

The CMCs, Delta CMCs, Efficiency, and Delta CMC/750 for Compositions (E9, E12, E13, E14, and E15) and comparable composition C1 with the surfactant cocamidopropyl betaine (CAPB) were calculated using the Forward Titration Tensiometry Test as described below and the results reported in Table 4.

The compositions were tested for Critical Micelle Concentration (CMC) values using the Forward Titration Tensiometry Test. The initial solution was 30 ml of one of the Examples. The dosing solution was 5750 mg/L of CAPB in HPLC grade water. Forty-two (42) doses were preformed, which increased the sodium trideceth concentration from 0 mg/L in the initial solution up to 3771 mg/L at the final measurement. The Delta CMCs for each composition were calculated based on the CMC for comparable composition C1 and such values were plotted as a function of polymer concentration in FIG. 4 as an illustration of the efficiency of the polymer to associate surfactant thereto (and reduce irritation).

TABLE 4

| Examples | PA-18 (mg/L) | CMC CAPB (mg/L) | Δ CMC CAPB (mg/L) | Efficiency | Δ CMC/750 CAPB % |
|---|---|---|---|---|---|
| | 0 | | na | na | na |
| | 50 | 309 | 254 | 5.1 | 11 |
| | 250 | 1225 | 1128 | 4.5 | 48 |
| | 350 | 1611 | 1481 | 4.2 | 63 |
| | 500 | 2100 | 1905 | 3.8 | 82 |
| | 750 | 2675 | 2333 | 3.1 | 100 |

Figure 4:
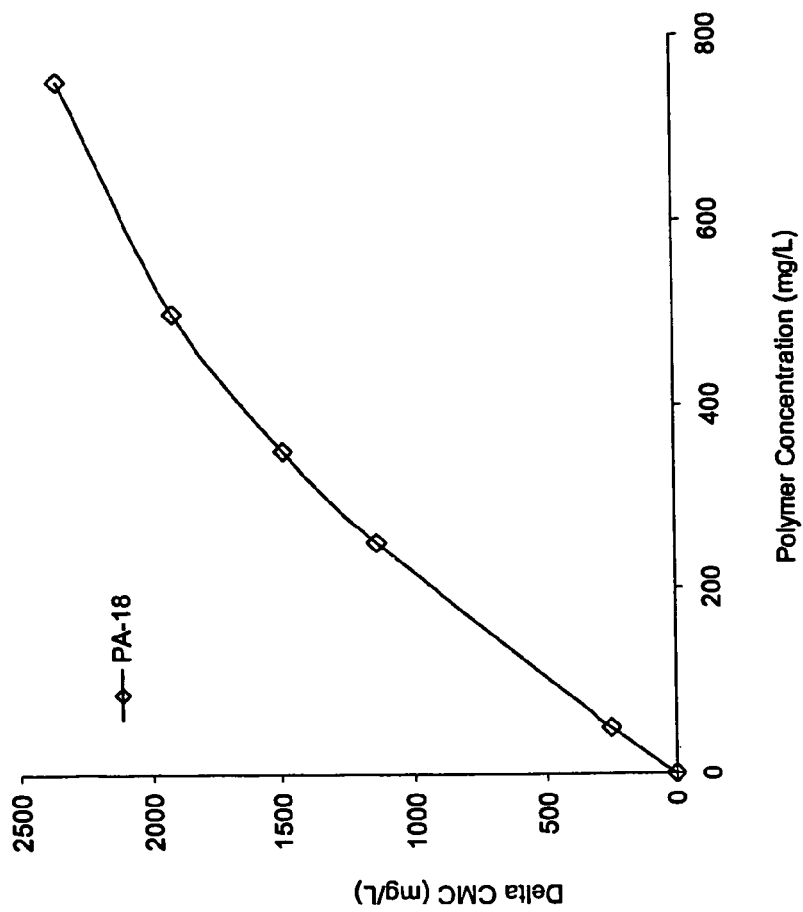
FIG. 4 is a graphical depiction of the relative efficiency of a polymer of the present invention to associate surfactant thereto according to another embodiment.

As shown in Table 4 and FIG. 4, the $C_{90}$ value associated with the PA-18 polymer and CAPB is greater than about 250 mg/L (and greater than 500 mg/L).

Example 4

This Example illustrates the low-irritation properties of the present invention compared to comparable high molecular weight compositions.

The compositions of the present invention E15 and E16 and comparative C9 were prepared according to the materials and amounts listed in Table 5.

Each of the compositions of Table 5 was independently prepared as follows: Water (50.0 parts) was added to a beaker. The polymer, (Inutec SP-1 in E15 and E16, and Carbopol Aqua SF1 in C9) was added to the water with mixing. The following ingredients were added thereto independently with mixing until each respective resulting mixture was homogenous: Tegobetaine L7V, Atlas G4280, Cedepal TD403LD, Glycerin 917, Dowicil 200, and Versene 100XL. The pH of the resulting solution was then adjusted with either a 20% Citric Acid solution or a 20% Sodium Hydroxide solution until a final pH of about 6.3 to 6.6 was obtained. The remainder of the water was then added thereto.

The compositions were then tested for mildness in accordance with the above TEP Test and the results listed in Table 6.

TABLE 6

| Example | TEP value |
|---|---|
| C9 | 3.19 ± 0.7 |
| E15 | 2.54 ± 0.6 |
| E16 | 3.64 ± 0.5 |

As seen in Table 6, in two formulas with equivalent amounts of Aqua SF-1 or Inutec SP-1, the formula with Inutec SP-1 was milder than the formula with Aqua SF-1. In both formulas, the polymer concentration is sufficiently high that the Aqua SF-1 has lost efficiency to associate TDES, while the Inutec SP-1 tends to not lose efficiency.

Example 5

This Example illustrates the low-irritation properties of the present invention compared to comparable high molecular weight compositions.

The compositions of the present invention E17 and E18 and comparative C10 were prepared according to the materials and amounts listed in Table 5.

TABLE 5

| Tradename | INCI Name | C9 | E15 | E16 |
|---|---|---|---|---|
| Inutec SP-1 | Inulin Lauryl Carbamate | — | 0.9 | 1.8 |
| Carbopol AQUA SF1 (30%) | Acrylates Copolymer | 6.0 | — | — |
| Tegobetaine L7V (30%) | Cocamidopropyl Betaine | 11.33 | 11.33 | 11.33 |
| Atlas G-4280 | PEG-80 Sorbitain Laurate | | | |
| Cedepal TD403LD (30%) | Sodium Trideceth Sulfate | 20.000 | 20.000 | 20.000 |
| Glycerin 917 (99%) | Glycerin | 1.900 | 1.900 | 1.900 |
| Dowicil 200 | Quaternium-15 | 0.050 | 0.050 | 0.050 |
| Versene 100XL | Tetrasodium EDTA | 0.263 | 0.263 | 0.263 |
| Water | Water | qs | Qs | qs |

TABLE 7

| Tradename | INCI Name | C10 | E17 | E18 |
|---|---|---|---|---|
| Inutec SP-1 | Inulin Lauryl Carbamate | — | 0.9 | 1.8 |
| Carbopol AQUA SF1 (30%) | Acrylates Copolymer | 6.0 | — | — |
| Tegobetaine L7V (30%) | Cocamidopropyl Betaine | 22.4 | 22.4 | 22.4 |
| Atlas G-4280 | PEG-80 Sorbitain Laurate | 2.00 | 2.00 | 2.00 |
| Cedepal TD403LD (30%) | Sodium Trideceth Sulfate | 16.00 | 16.00 | 16.00 |
| Polyox WSR N-60K | PEG-45M | 0.075 | 0.075 | 0.075 |
| Sodium Benzoate NF | Sodium benzoate | 0.50 | 0.50 | 0.50 |
| Versene 100XL | Tetrasodium EDTA | 0.25 | 0.25 | 0.25 |
| Water | Water | qs | Qs | Qs |

Each of the compositions of Table 7 was independently prepared as follows: Water (50.0 parts) was added to a beaker. The polymer, (Inutec SP-1 or Carbopol Aqua SF1) was added to the water with mixing. The following ingredients were added thereto independently with mixing until each respective resulting mixture was homogenous: Tegobetaine L7V, Atlas G-4280, Cedepal TD403LD, Polyox WSR-N, Sodium Bezoate, and Versene 100XL. The pH of the resulting solution was then adjusted with either a 20% Citric Acid solution or a 20% Sodium Hydroxide solution until a final pH of about 6.3 to 6.6 was obtained. The remainder of the water was then added thereto.

The were then tested for mildness in accordance with the above TEP Test and the results listed in Table 8.

TABLE 8

| Example | TEP value |
|---|---|
| C10 | 2.1 ± 0.3 |
| E17 | 2.3 ± 0.4 |
| E18 | 2.5 ± 0.3 |

As seen in Table 8, in two formulas with equivalent amounts of Aqua SF-1 or Inutec SP-1, the formula with Inutec SP-1 was milder than the formula with Aqua SF-1. In both formulas, the polymer concentration is sufficiently high that the Aqua SF-1 has lost efficiency to associate TDES, while the Inutec SP-1 tends to not lose efficiency.

Example 6

This Example illustrates the low-irritation properties of the present invention compared to comparable high molecular weight compositions.

Comparative compositions C11-C16 were prepared according to the materials and amounts listed in Table 9.

TABLE 9*

| | INCI Name | C11 | C12 | C13 | C14 | C15 | C16 |
|---|---|---|---|---|---|---|---|
| Carbopol Aqua SF-1 (30%) | Acrylates Copolymer | — | 0.900 | 2.700 | 3.600 | 4.500 | 6.000 |
| Atlas G-4280 (72%) | PEG-80 Sorbitan Laurate | 4.580 | 4.580 | 4.580 | 4.580 | 4.580 | 4.580 |
| Tegobetaine L7V (30%) | Cocamidopropyl Betaine | 11.330 | 11.330 | 11.330 | 11.330 | 11.330 | 11.330 |
| Cedepal TD403LD (30%) | Sodium Trideceth Sulfate | 20.000 | 20.000 | 20.000 | 20.000 | 20.000 | 20.000 |
| Glycerin 917 (99%) | Glycerin | 1.900 | 1.900 | 1.900 | 1.900 | 1.900 | 1.900 |
| Polymer JR-400 | Polyquaternium-10 | 0.140 | 0.140 | 0.140 | 0.140 | 0.140 | 0.140 |
| Dowicil 200 | Quaternium-15 | 0.050 | 0.050 | 0.050 | 0.050 | 0.050 | 0.050 |
| Versene 100XL | Tetrasodium EDTA | 0.263 | 0.263 | 0.263 | 0.263 | 0.263 | 0.263 |
| Water | Water | qs | qs | Qs | qs | qs | qs |

*expressed in % w/w

Each of the compositions of Table 9 was independently prepared as follows: Water (50.0 parts) was added to a beaker. For examples C12 through C16, Carbopol Aqua SF-1 was added to the water with mixing. (For Example C11, this step was omitted.) The Atlas G-4280 was then added thereto with mixing. The following ingredients were then added thereto independently with mixing until each respective resulting mixture was homogenous: Tegobetaine L7V, Cedepal TD403LD, Glycerin 917, Polymer JR400, Dowicil 200, and Versene 100XL. The pH of the resulting solution was then adjusted with either a 20% Sodium Hydroxide solution or a 20% Citric Acid solution until a final pH of about 6.3 to 6.6 was obtained. The remainder of the water was then added thereto.

Comparative compositions C11-C16 were then tested for mildness in accordance with the above TEP Test and the results listed in Table 10.

TABLE 10

| Example | TEP value | Delta TEP Value |
| --- | --- | --- |
| Example C14 | 1.46 ± 0.26 | — |
| Example C15 | 2.68 ± 0.28 | 1.22 |
| Example C16 | 2.85 ± 0.51 | 1.39 |
| Example C17 | 2.74 ± 0.18 | 1.28 |
| Example C18 | 3.34 ± 0.83 | 1.88 |
| Example C19 | 3.26 ± 0.39 | 1.80 |

Inulin/SLES

Compositions E19-E20 and comparable composition C 20 were prepared according to the materials and amounts listed in Table 11.

TABLE 11*

| Trade Name | CTFA Name (%) | C20 | E19 | E20 |
| --- | --- | --- | --- | --- |
| Inutec SP-1 | Inulin Lauryl Carbamate | — | 0.50 | 1.00 |
| Polymer JR 400 | Polyquaternium-10 (>97%) | 0.20 | 0.20 | 0.20 |
| Texapon NA | Sodium Laureth Sulfate (70%) | 7.14 | 7.14 | 7.14 |
| Empigen CDL 30/J/35 | Sodium-Lauroamphoacetate (27%) | 12.19 | 12.19 | 12.19 |
| Emery 917 Glycerin | Glycerin (99.7%) | 2.00 | 2.00 | 2.00 |
| PEG-150 Distearate | PEG-150 Distearate | 0.10 | 0.10 | 0.10 |
| Luviquat Ultra Care | Polyquaternium-44 | 1.50 | 1.50 | 1.50 |
| Plantacare UP | Coco-Glucoside (55%) | 7.46 | 7.46 | 7.46 |
| RO-1399 | Fragrance | 0.20 | 0.20 | 0.20 |
| Atlas G-4280 | POE-80 Sorbitan Lautrate (72%) | 0.80 | 0.80 | 0.80 |
| Tween 20 | Polysorbate 20 (>95%) | 0.10 | 0.10 | 0.10 |
| Tocpherol Acetate | Tocpherol Acetate | 0.10 | 0.10 | 0.10 |
| Extrapone *Aloe Vera* | *Aloe Vera* | 0.10 | 0.10 | 0.10 |
| Versene NA | Tetrasodium EDTA (86%)/Sodium salt (8%) | 0.076 | 0.076 | 0.076 |
| Sodium Benzoate | Sodium Benzoate | 0.50 | 0.50 | 0.50 |
| Lamesoft ™ Benz | Glycol distearate/Coco-Glucoside/Glyceryl oleate/Glyceryl stearate | 5.00 | 5.00 | 5.00 |
| Citric acid | Citric Acid (92%) | 1.08 | 1.08 | 1.08 |
| Water | Water | q.s. | q.s. | q.s. |

*expressed in % w/w

Each of the compositions of Table 11 was independently prepared as follows: Water (50.0 parts) was added to a beaker. For examples E19 and E20, Inutec SP-1 was added to the water with mixing. (For Example C20, this step was omitted.) The Atlas G-4280 was then added thereto with mixing. The following ingredients were then added thereto independently with mixing until each respective resulting mixture was homogenous: Texapon, Empigen, Polymer JR 400, Glycerin 917, PEG-150 Distearate, Luviquat Ultra Care, Plantacare UP, Fragrance, Tween 20, Tocpherol Acetate, Extrapone Aloe Vera, Versene, Sodium Benzoate and Lamesoft Benz. The pH of the resulting solution was then adjusted with a 20% solution of Citric Acid solution until a final pH of about 6.3 to 6.6 was obtained. The remainder of the water was then added thereto.

Compositions E19, E20, and C20 were then tested for mildness in accordance with the above TEP Test and the results listed in Table 12.

TABLE 12

| Example | TEP value |
| --- | --- |
| C20 | 1.05 ± 0.05 |
| E19 | 1.5 ± 0.4 |
| E20 | 3.0 ± 0.3 |

PA-18/CAPB

Compositions E21-E22 and comparable composition C21 were prepared according to the materials and amounts listed in Table 13.

TABLE 13*

| Trade Name | CTFA Name (%) | C21 | E21 | E22 |
|---|---|---|---|---|
| Cocamidopropyl Betaine | Tegobetaine L7-V (30%) | 7.2 | 7.2 | 6.0 |
| Octadecene/MA Copolymer | PA-18, LV-Commercial, solution (26%) | — | 4.8 | 4.8 |
| parabens | Nipasept Sodium | 0.30 | 0.30 | 0.30 |
| Tetrasodium EDTA | Versene 100XL (50%) | 0.25 | 0.25 | 0.25 |
| Citric Acid | Citric Acid Solution, (20%) | q.s. | q.s. | q.s. |
| Sodium Hydroxide | Sodium Hydroxide (20%) | q.s. | q.s. | q.s. |
| Water | Water | q.s. | q.s. | q.s. |

*expressed in % w/w

Each of the compositions of Table 13 was independently prepared as follows: Water (50.0 parts) was added to a beaker. PA-18 was added (for E21 and E22 only). The following ingredients were then added thereto independently with mixing until each respective resulting mixture was homogenous: Sodium Benzoate. The pH of the resulting solution was then adjusted with a 20% solution of Citric Acid solution until a final pH of about 6.3 to 6.6 was obtained. The remainder of the water was then added thereto.

Compositions E-21, E22, and C21 were then tested for mildness in accordance with the above TEP Test and the results listed in Table 14.

TABLE 14

| Example | TEP value | Delta TEP |
|---|---|---|
| C21 | 2.55 ± 0.46 | n.a. |
| E21 | 4.76 ± 0.66 | 2.21 |
| E22 | 5.51 ± 0.20 | — |

PA-18/TDES

Composition E23 and comparable composition C22 were prepared according to the materials and amounts listed in Table 15.

TABLE 15*

| Trade Name | CTFA Name (%) | C22 | E23 |
|---|---|---|---|
| PA-18, LV-Commercial | Octadecene/MA Copolymer, solution (25%) | — | 7.2 |
| Cedepal TD403MF-LD | Sodium Trideceth Sulfate (30%) | 16 | 16 |
| Tegobetaine L7-V | Cocamidopropyl Betaine (30%) | 22.4 | 22.4 |
| Fragrance RO-1399 | Fragrance | 0.50 | 0.50 |
| Crodacel QM | PG-HEC Cocadimonium Chloride (20%) | 0.75 | 0.75 |
| Crodacel QS | PG-HEC Stearyldimonium Chloride (20%) | 0.25 | 0.25 |
| Versene 100XL | Tetrasodium EDTA (38%) | 0.25 | 0.25 |
| Nipasept Sodium | Sodium Methyl, Ethyl, Propyl-Paraden (16%) | 0.30 | 0.30 |

TABLE 15*-continued

| Trade Name | CTFA Name (%) | C22 | E23 |
|---|---|---|---|
| Citric Acid | Citric Acid Solution, (20%) | q.s. | q.s. |
| Sodium Hydroxide | Sodium Hydroxide (20%) | q.s. | q.s. |
| Water | Water | q.s. | q.s. |

*expressed in % w/w

Each of the compositions of Table 15 was independently prepared as follows: Water (50.0 parts) was added to a beaker. For E23, PA-18 was added. The following ingredients were then added thereto independently with mixing until each respective resulting mixture was homogenous: Cedepal TD403MF-D, Tegobetaine L7-V, Crodacel QM, Crodacel QS, Versene 100XL, and Nipasept. The pH of the resulting solution was then adjusted with a 20% solution of Citric Acid solution until a final pH of about 6.3 to 6.6 was obtained. The remainder of the water was then added thereto.

Compositions E23 and C22 were then tested for mildness in accordance with the above TEP Test and the results listed in Table 16.

TABLE 16

| Example | TEP value | Delta TEP |
|---|---|---|
| C22 | 1.9 ± 0.4 | n.a. |
| E23 | 2.4 ± 0.7 | 0.5 |

Example 7

This Example illustrates the desirable rheological and aesthetic properties associated with certain compositions of the present invention as compared to comparative compositions. All rheological measurements were conducted on a TA Instruments AR 2000 Rheometer (New Castle, Del.). The geometry used was double gap concentric cylinders with a gap of 500 μm and an outer radius of 20 mm. All rheological measurements were preformed at 25° C., and a solvent trap was used to minimize evaporation during the experiment. Compositions E24, C23 and C24 were prepared according to the materials and amounts listed in Table 17. The viscosity of each such composition was measured and the results reported in Table 18.

TABLE 17

| Tradename | INCI Name | C23 | E24 | C24 |
|---|---|---|---|---|
| Inutec SP-1 | Inulin Lauryl Carbamate | — | 1.8 | — |
| Carbopol AQUA SF1 (30%) | Acrylates Copolymer | — | — | 6.0 |
| Tegobetaine L7V (30%) | Cocamidopropyl Betaine | 11.33 | 11.33 | 11.33 |
| Atlas G-4280 | PEG-80 Sorbitain Laurate | | | |
| Cedepal TD403LD (30%) | Sodium Trideceth Sulfate | 20.00 | 20.00 | 20.00 |
| Glycerin 917 (99%) | Glycerin | 1.900 | 1.900 | 1.900 |

TABLE 17-continued

| Tradename | INCI Name | C23 | E24 | C24 |
|---|---|---|---|---|
| Dowicil 200 | Quaternium-15 | 0.050 | 0.050 | 0.050 |
| Versene 100XL | Tetrasodium EDTA | 0.263 | 0.263 | 0.263 |
| Water | Water | qs | Qs | Qs |

TABLE 18

| | Viscosity | | |
|---|---|---|---|
| Shear rate (1/s) | C23 (poise) | E24 (poise) | C24 (poise) |
| 0.051 | 0.14 | 0.72 | 137 |
| 1.0 | 0.38 | 0.80 | 30 |
| 5.0 | 0.35 | 0.81 | 15 |
| 10 | 0.35 | 0.81 | 12 |
| 101 | 0.35 | 0.80 | 7.0 |
| 1007 | 0.33 | 0.73 | 4.0 |

Figure 10:
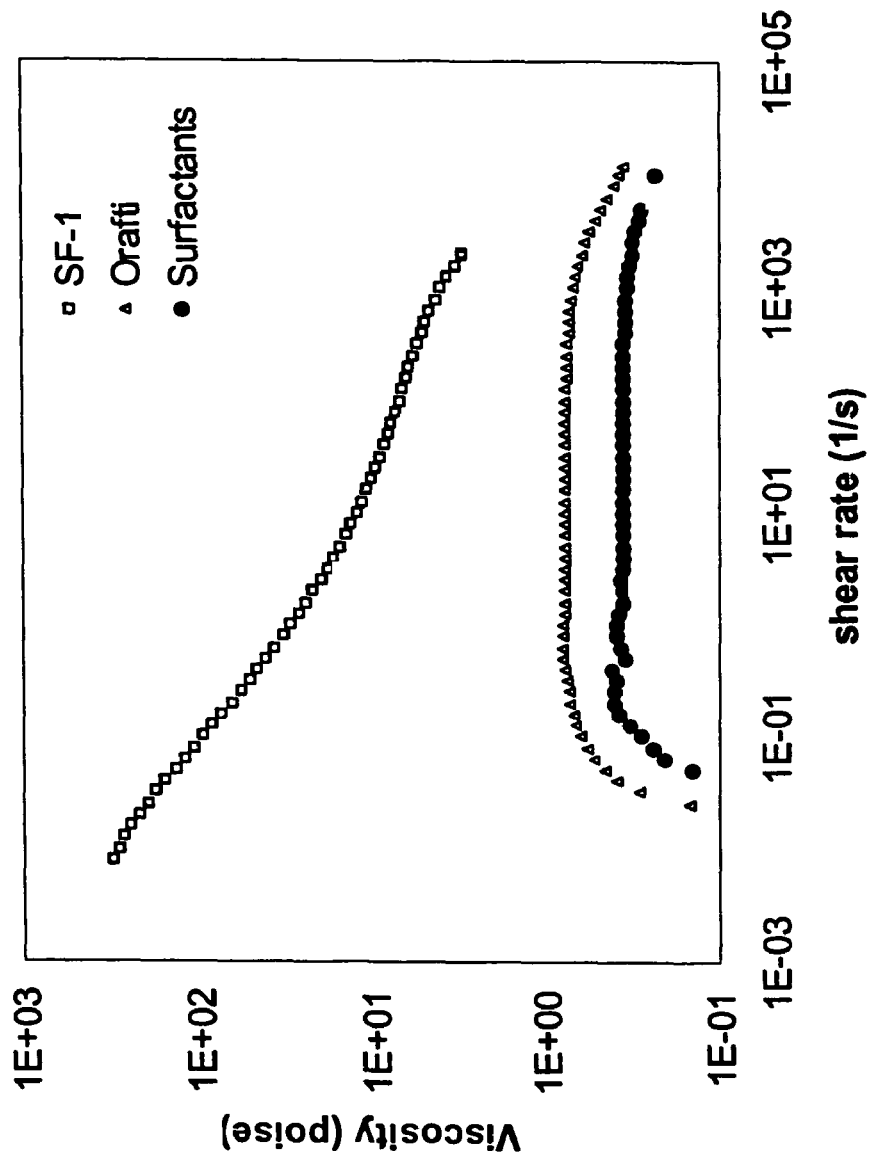
FIG. 10 is a graphical depiction of the rheology data associated with a composition of the present invention.

As seen in Table 18, the magnitude of the viscosity of the surfactant base (C23) is similar to that of the surfactant base with Inutec SP-1 (E24). Additionally the viscosities of both C23 and E24 are independent of the shear rate. Conversely the viscosity of C24 is significantly higher and is shear thinning. For instance at a shear rate of 1/s, EW24 with Inutec SP-1 has a viscosity of 0.80 poise, while C24 with SF-1 has a viscosity of 30 poise. The addition of SF-1 has a significant effect on the rheology of the formula, while the addition of Inutec SP-1 has a minimal effect on the rheology. Reference is made to FIG. 10 showing curves of the related to this viscosity data.

Example 8

An industrially accepted means to measure the foam generation of the consumer product is the Sita Foam Tester R-2000 (SITA Messtechnik GmbH, Dresden Germany). Specifically designed to measure foam generation, the Sita Foam Tester consists of a jacketed sample vessel with and agitator. To represent the hard water of tap water, 0.36 g of calcium chloride is dissolved in 995 g of DI water. Five (5) grams of test formula is added to this solution and mixed until homogeneous. Then this 0.5% dilution of test formula is placed in the holding tank of the Sita Foam Tester. For each experimental run, 250 ml of solution is introduced into the test vessel and allowed to come to 30° C.±2° C. The agitator spins at 1300 rpm for 30 seconds, then the foam volume is measured. The agitation is repeated for a total of 9 cycles. The foam generation test is conducted 3 times for each test sample.

Compositions E19, E20, C20, and C24 were tested via the above procedure and the foam volume at 90 seconds and the $F_{max}$ for each is measured and reported in Table 19.

TABLE 19

| Formula | Foam Vol. (ml @ 90 s) | Foam Vol. (ml @ max) ($F_{max}$) |
|---|---|---|
| C20 (inutec 0%) | 300 ± 2 | 351 ± 8 |
| E19 (inutec 0.5%) | 324 ± 12 | 360 ± 1 |
| E20 (Inutec 1%) | 324 ± 17 | 366 ± 4 |
| C24 | 317 ± 63 | 350 ± 41 |
| E21 | 289 ± 6 | 393 ± 22 |

Example 9

A composition is made as in E18 except that a low molecular weight hydrophobically-modified acrylic polymer derived from at least one unsaturated carboxylic acid monomer; at least one hydrophobic monomer; a hydrophobic chain transfer agent comprising one or more alkyl mercaptans, thioesters, amino acid-mercaptan-containing compounds, peptide fragments, or combinations thereof; a cross-linking agent; and, optionally, a steric stabilizer; wherein the amount of said unsaturated carboxylic acid monomer is from about 60% to about 98% by weight based upon the total weight of said unsaturated monomers and said hydrophobic monomer is used in place of the Inutec SP-1. The CMC and TEP properties are measured and indicate reduced irritation properties that at least as good or better than those of the E18 Inutec SP-1 composition.

Example 10

A composition is made as in E18 except that a low molecular weight hydrophobically-modified associative macromer having a backbone derived from methacrylate and ethylacrylate, and a hydrophobic portion derived from itaconate monomers, which polymer is made via emulsion polymerization is used in place of the Inutec SP-1. The CMC and TEP properties are measured and indicate reduced irritation properties that at least as good or better than those of the E18 Inutec SP-1 composition.

Example 11

This example illustrates a hydrolysis procedure for preparing 12.5% hydrolyzed PA-18 solution.

To a 800 mL Pyrex beaker equipped with a stainless steel mixing blade, hotplate, and thermometer was charged 441 g deionized water. The solution was heated and mixed at medium speed, and 12.6 g sodium hydroxide pellets were slowly added to the vessel. At 65° C., 50.0 g of Octadecene [e]/MA Copolymer (PA-18, Low Viscosity Commercial grade, Chevron Phillips Chemical) was slowly sifted into the solution to obtain a uniform opaque yellowish-white dispersion. The dispersion was heated to 90-95° C., covered, and mixed at high speed for one hour to obtain complete hydrolysis of the copolymer. Hydrolysis was indicated by dissolution of the dispersed polymer and the formation of a hazy, transparent yellow solution. The hydrolyzed copolymer solution was cooled to ambient temperature while mixing at medium speed and deionized water added in q.s. to 100%. Final pH=11.1 and solids content=12.5%.

What is claimed is:

1. A composition comprising a low molecular weight polymeric material selected from the group consisting of polysaccharide polymers derived from starch, inulin, guar, xanthan, carrageenan, chitosan, pectin, or schizophyllan, such polymers having a molecular weight of from about 3,500 to about 500,000 g/mol, and an alternating octadecene/maleic anhydride copolymer having a molecular weight of from about 20,000 to about 25,000 and capable of binding a surfactant thereto and at least one surfactant selected from the group consisting of anionic surfactants in an amount of from about 0.1 to about 12.5 weight % active surfactant in composition, amphoteric surfactants, and combinations of two or more thereof, said composition having a Delta CMC of at least about 80.

2. The composition of claim 1 wherein said low molecular weight polymeric material is a hydrophobically-modified polysaccharide polymer derived from starch, inulin, guar, xanthan, carrageenan, chitosan, pectin, or schizophyllan that has a molecular weight of from about 3,500 to about 100,000 g/mol.

3. The composition of claim 1 wherein said low molecular weight polymeric material and surfactant exhibit a $C_{90}$ value of greater than 250 mg/L.

4. The composition of claim 1 wherein said low molecular weight polymeric material and surfactant exhibit a $C_{90}$ value of greater than 300 mg/L.

5. The composition of claim 1 wherein said low molecular weight polymeric material and surfactant exhibit a $C_{90}$ value of greater than 450 mg/L.

6. The composition of claim 1 wherein said composition has a Delta CMC of at least about 300.

7. The composition of claim 1 wherein said composition has a TEP of at least about 1.5 or greater.

8. The composition of claim 1 wherein said composition has a TEP of at least about 2 or greater.

9. The composition of claim 1 wherein said composition has a TEP of at least about 3 or greater.

10. The composition of claim 1 wherein said low molecular weight polymeric material comprises a polymer selected from the group consisting of hydrophobically-modified starches, hydrophobically-modified inulins and combinations of two or more thereof.

11. The composition of claim 1 wherein said low molecular weight polymeric material comprises an alternating octadecene/maleic anhydride copolymer, having a molecular weight of from about 20,000 to about 25,000.

12. The composition of claim 1 wherein said low molecular weight polymeric material comprises a hydrophobically-modified inulin polysaccharide.

13. The composition of claim 1 wherein said at least one surfactant comprises at least one anionic surfactant selected from the group consisting of sodium trideceth sulfate, sodium laureth sulfate, and combinations thereof.

14. The composition of claim 1 wherein said at least one surfactant comprises at least one amphoteric surfactant.

15. The composition of claim 13 wherein said at least one amphoteric surfactant comprises a betaine surfactant.

16. The composition of claim 15 having an $F_{max}$ of at least about 300 ml.

17. A method of treating at least a portion of the human body comprising contacting the body with a composition of claim 1.

18. A method of cleansing at least a portion of the human body with reduced irritation comprising contacting the body with a composition of claim 1.

19. A method of treating at least a portion of the human body comprising contacting the body with a composition of claim 15.

20. A method of cleansing at least a portion of the human body with reduced irritation comprising contacting the body with a composition of claim 15.

21. A composition comprising a low molecular weight polymeric material selected from the group consisting of polysaccharide polymers derived from starch, inulin, guar, xanthan, carrageenan, chitosan, pectin, or schizophyllan, such polymers having a molecular weight of from about 3,500 to about 500,000 g/mol and an alternating octadecene/maleic anhydride copolymer having a molecular weight of from about 20,000 to about 25,000 and capable of binding a surfactant thereto and at least one anionic surfactant selected from the group consisting of alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof, said composition having a Delta CMC of at least about 80.

22. The composition of claim 21 wherein said low molecular weight polymeric material is a hydrophobically-modified polysaccharide polymer derived from starch, inulin, guar xanthan, carrageenan, chitosan, pectin, or schizophyllan that has a molecular weight of from about 3,500 to about 100,000 g/mol.

23. The composition of claim 21 wherein said low molecular weight polymeric material is a hydrophobically-modified inulin polysaccharide or an alternating octadecene/maleic anhydride copolymer, having a molecular weight of from about 20,000 to about 25,000.

24. The composition of claim 21 wherein said at least one anionic surfactant comprises at least one surfactant selected from the group consisting of sodium trideceth sulfate, sodium laureth sulfate, and combinations thereof.

25. The composition of claim 21 wherein said composition further comprises at least one amphoteric surfactant.

26. A composition comprising a low molecular weight polymeric material selected from the group consisting of polysaccharide polymers derived from starch, inulin, guar, xanthan, carrageenan, chitosan, pectin, or schizophyllan, such polymers having a molecular weight of from about 3,500 to about 100,000 g/mol and an alternating octadecene/maleic anhydride copolymer having a molecular weight of from about 20,000 to about 25,000 and capable of binding a surfactant thereto and at least one amphoteric surfactant, said composition having a Delta CMC of at least about 80.

27. The composition of claim 26 wherein said low molecular weight polymeric material is a hydrophobically-modified polysaccharide polymer derived from starch, inulin, guar xanthan, carrageenan, chitosan, pectin, or schizophyllan that has a molecular weight of from about 3,500 to about 100,000 g/mol.

28. The composition of claim 26 wherein said low molecular weight polymeric material is a hydrophobically-modified inulin polysaccharide or an alternating octadecene/maleic anhydride copolymer, having a molecular weight of from about 20,000 to about 25,000.

29. The composition of claim 26 wherein said at least one amphoteric comprises a betaine.

30. The composition of claim 26 further comprising an anionic surfactant.

31. A method of cleansing at least a portion of the human body comprising contacting the body with a composition of claim 21.

32. A method of cleansing at least a portion of the human body comprising contacting the body with a composition of claim 26.

* * * * *